US008877942B2

(12) United States Patent
Filatov et al.

(10) Patent No.: US 8,877,942 B2
(45) Date of Patent: Nov. 4, 2014

(54) 2,2'-DISUBSTITUTED DIPYRRIN COMPOUNDS, SYNTHESIS THEREOF AND METHODS OF USE THEREOF

(75) Inventors: Mikhail Filatov, Moscow (RU); Andrei Cheprakov, Moscow (RU); Sergei A. Vinogradov, Wynewood, PA (US); Artem Y. Lebedev, Culver City, CA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 12/902,401

(22) Filed: Oct. 12, 2010

(65) Prior Publication Data

US 2011/0144351 A1    Jun. 16, 2011

Related U.S. Application Data

(60) Provisional application No. 61/250,201, filed on Oct. 9, 2009.

(51) Int. Cl.

| C07F 3/06 | (2006.01) |
|---|---|
| C07F 3/08 | (2006.01) |
| C07D 403/06 | (2006.01) |
| C07D 209/62 | (2006.01) |
| C07F 3/00 | (2006.01) |
| C07D 209/44 | (2006.01) |

(52) U.S. Cl.
CPC .............. *C07D 209/62* (2013.01); *C07F 3/003* (2013.01); *C07D 209/44* (2013.01)
USPC .......................................... 548/402; 548/518

(58) Field of Classification Search
USPC ................. 424/426; 435/68.1, 183; 536/23.4; 548/216, 417
See application file for complete search history.

(56) References Cited

U.S. PATENT DOCUMENTS

| 5,433,896 | A | 7/1995 | Kang et al. |
|---|---|---|---|
| 6,005,113 | A | 12/1999 | Klaubert et al. |
| 6,759,144 | B2 | 7/2004 | Toguchi et al. |
| 6,805,978 | B2 | 10/2004 | Murase et al. |
| 6,921,589 | B2 | 7/2005 | Kohama et al. |
| 6,924,375 | B2 * | 8/2005 | Lindsey et al. ............... 548/108 |

OTHER PUBLICATIONS

Shen, et al., Chem. Eur. J., 2004, vol. 10, pp. 4853-4871.*
Wood, et al., Chem. Rev., 2007, 107, 1831-1861. See IDS Submitted Jun. 25, 2012, p. 2 of 4, Reference #2.*
Zhan, et al., J. Phys. Chem. B, 2003, 107, 2853-2861.*
Chemical Abstract Registry No. 1097623-16-9, indexed in the Registry File on STN CAS Online Jan. 29, 2009.*
S. Nanya, H. Osawa, K. Obata and E. Maekawa, Synthesis of Dibenzopyrromethene Pigments from 1-Phenylisoindole *Nippon Kagaku Zasshi*, 91, 181-& (1970). (English abstract).
I. K. Svirenski, Molecular Complexes of (1-Aryl-3-Isoindolyl) (1-Aryl-3-Pseudoisoindolenylidene) Arylmethanes with Some Organic and Inorganic Acids *Dokladi Na Bolgarskata Akademiya Na Naukite*, 26, 203-205 (1973).
S. Mincev, I. K. Svirenski and B. V. Aleksiev, New Possibility for Synthesis of (1-Aryl-3-Isoindolyl)-(1-Aryl-3-Pseudoisoindolenylidene)-Arylmethanes *Dokladi Na Bolgarskata Akademiya Na Naukite*, 26, 1629-1632 (1973). (English abstract).
S. Kirschenbaum and M. D. Glantz, 2,3-Diphenyl-1-Indanone Fluorometric Analysis of Amino-Acids *Mikrochimica Acta*, 1, 589-598 (1976).
E. Maekawa, Constitution of Dyes from O-Acyl Benzophenone and Ammonia *Chemische Berichte*, 101, 847-& (1968). English abstract.
G. Struckmeier, J. Engel and U. Thewalt, Crystal and Molecular-Structure of 5,5'-Diethoxycarbonyl-3,3'-Diethyl-4,4'-Dimethyl-Pyrromethene Hydrobromide *Zeitschrift Fur Naturforschung Section B—a Journal of Chemical Sciences*, 33, 753-755 (1978). (English abstract).
W. S. Sheldrick, A. Borkenstein, G. Struckmeier and J. Engel, 5,5'-Diethoxycarbonyl-3,3'-Diethyl-4,4'-Dimethyl-2,2'-Pyrromethene *Acta Crystallographica Section B—Structural Science*, 34, 329-332 (1978).
Fischer, H.; Schubert, M. *Ber. Dtsch. Chem. Ges.* 1924, 57, 610-617. (English abstract).
Fischer, H.; Klarer, J. *Justus Liebigs Ann. Chem.* 1926, 448, 178-193. (English abstract).
E. T. Clarke, P. J. Squattrito, P. R. Rudolf, R. J. Motekaitis, A. E. Martell and A. Clearfield, Structural Investigations of the Dipyrromethene Complexes of Calcium(Ii), Nickel(Ii) and Copper(Ii) *Inorganica Chimica Acta*, 166, 221-231 (1989).
G. Ulrich, R. Ziessel and A. Harriman, The chemistry of fluorescent bodipy dyes: Versatility unsurpassed *Angewandte Chemie—International Edition*, 47, 1184-1201 (2008).
T. E. Wood and A. Thompson, Advances in the chemistry of dipyrrins and their complexes *Chemical Reviews*, 107, 1831-1861 (2007).
J. D. White, M. E. Mann, Kirshenb.Hd and A. Mitra, Condensation of 1,2-Dibenzoylcyclohexa-1,4-Dienes—Synthesis of 1,3-Diphenyl-Substituted Isoindoles, Isobenzofurans, and Isobenzothiophenes *Journal of Organic Chemistry*, 36, 1048-& (1971).
J. C. Emmett and W. Lwowski, 1,3-Diphenylisoindoles *Tetrahedron*, 22, 1011-& (1966).
T. P. Ivanov, Action of Ammonia on Arylsubstituted Indones in Absence of Metal Salts *Monatshefte Fur Chemie*, 99, 1990-& (1968). Abstract only.
I. K. Svirenski and P. Petrov, Electrical Conductivity of Some Molecular Complexes of (1-Aryl-3-Isoindolyl-)-(1-Aryl-3-Pseudoisoindolenyliden)-Arylmethanes and Their Iodine and Bromine Derivatives *Monatshefte Fur Chemie*, 104, 68-73 (1973). Abstract only.
G. M. Brown, R. G. Curtis, W. Davies, T. A. Dopheide, Hawthorn.Dg, J. R. Hlubucek, B. M. Holmes, J. F. Kefford, J. L. Osborne, Robertso. Av and E. C. Slater, Structure of an Isoindole Pigment from Interaction of Phenylmagnesium Bromide and Trans-O-Cyano-Beta-Bromostyrene *Australian Journal of Chemistry*, 21, 483-& (1968).

(Continued)

*Primary Examiner* — Michael Barker
*Assistant Examiner* — Po-Chih Chen
(74) *Attorney, Agent, or Firm* — Mark S. Cohen; Pearl Cohen Zedek Latzer Baratz LLP

(57) ABSTRACT

The present invention relates to 2,2'-di-substituted dipyrrins. The invention also relates to methods for the preparation of 2,2'-disubstituted dipyrrins, and to the use of 2,2'-disubstituted dipyrrins in, for example, sensing, imaging and laser applications.

16 Claims, 7 Drawing Sheets

(56) References Cited

OTHER PUBLICATIONS

C. O. Bender, R. Bonnett and R. G. Smith, Formation of Metal Octamethyltetrabenzporphyrins from Isoindole Precursors *Journal of the Chemical Society—Perkin Transactions 1*, 771-& (1972).

S. Nanya and E. Maekawa, Pigment Formation by Reaction of Ortho Acetylbenzophenone with Cyclohexylamine *Nippon Kagaku Kaishi*, 770-& (1972). Abstract only.

S. Nanya and E. Maekawa, Structures of Pigments Formed by Reaction of Ortho-Acetylbenzophenone with Aliphatic Primary Amines *Nippon Kagaku Kaishi*, 1953-1956 (1974). Abstract only.

S. Nanya and E. Maekawa, Pigments Formed by Reaction of Ortho-Acetylbenzophenone with Aniline and Alpha-Branched Primary Amines *Nippon Kagaku Kaishi*, 1535-1540 (1975). Abstract only.

S. Nanya and E. Maekawa, Color-Reactions of Ortho-Acetylbenzophenone with Amino-Acids *Nippon Kagaku Kaishi*, 1750-1751 (1977). Abstract only.

S. Nanya, T. Kitahara, T. Kuroda and Y. Butsugan, Isoindole Derivatives from 2-Isonicotinoyl-Acetophenone with Ammonia and Its Derivatives *Journal of Heterocyclic Chemistry*, 29, 1301-1303 (1992).

M. Wada, S. Ito, H. Uno, T. Murashima, N. Ono, T. Urano and Y. Urano, Synthesis and optical properties of a new class of pyrromethene-BF2 complexes fused with rigid bicyclo rings and benzo derivatives *Tetrahedron Letters*, 42, 6711-6713 (2001).

Y. H. Yu, A. B. Descalzo, Z. Shen, H. Rohr, Q. Liu, Y. W. Wang, M. Spieles, Y. Z. Li, K. Rurack and X. Z. You, Mono- and di(dimethylamino) styryl-substituted borondipyrromethene and borondiindomethene dyes with intense near-infrared fluorescence *Chemistry—an Asian Journal*, 1, 176-187 (2006).

G. Ulrich, S. Goeb, A. De Nicola, P. Retailleau and R. Ziessel, Synthesis of bisisoindolomethene dyes bearing anisole or ethylthiophene residues for red and near-IR fluorescence *Synlett*, 1517-1520 (2007).

J. Chen, A. Burghart, A. Derecskei-Kovacs and K. Burgess, 4,4-difluoro-4-bora-3a,4a-diaza-s-indacene (BODIPY) dyes modified for extended conjugation and restricted bond rotations *Journal of Organic Chemistry*, 65, 2900-2906 (2000).

A. B. Descalzo, Phenanthrene-fused boron-dipyrromethenes as bright long-wavelength fluorophores *Org Lett*, 10, 1581-1584 (2008).

K. Umezawa, Y. Nakamura, H. Makino, D. Citterio and K. Suzuki, Bright, color-tunable fluorescent dyes in the visible-near-infrared region *Journal of the American Chemical Society*, 130, 1550-+ (2008).

W. L. Zhao and E. M. Carreira, Conformationally restricted Aza-BODIPY: Highly fluorescent, stable near-infrared absorbing dyes *Chemistry—a European Journal*, 12, 7254-7263 (2006).

I. V. Sazanovich, C. Kirmaier, E. Hindin, L. H. Yu, D. F. Bocian, J. S. Lindsey and D. Holten Structural control of the excited-state dynamics of bis(dipyrrinato)zinc complexes: Self-assembling chromophores for light-harvesting architectures *J. Am. Chem. Soc.* 2004; 126: 2664-2665.

J. M. Sutton, E. Rogerson, C. J. Wilson, A. E. Sparke, S. J. Archibald and R. W. Boyle, Synthesis and structural characterisation of novel bimetallic dipyrromethene complexes: rotational locking of the 5-aryl group *Chemical Communications*, 1328-1329 (2004).

V. S. Thoi, J. R. Stork, D. Magde and S. M. Cohen, Luminescent dipyrrinato complexes of trivalent group 13 metal ions *Inorganic Chemistry*, 45, 10688-10697 (2006).

A. H. Corwin and M. H. Melville, Relative Stabilities of Chelate Compounds of Pyrrole Pigments *Journal of the American Chemical Society*, 77, 2755-2759 (1955).

R. J. Motekaitis and A. E. Martell, Halogenated Symmetrical Dipyrromethene Chelates *Inorganic Chemistry*, 9, 1832-& (1970).

F. C. March, Dipyrromethene Complexes of Transition Metals .2. Stereochemistry of Complexes of Cobalt(Ii), Nickel(Ii), Copper(Ii), Zinc(Ii), Cadmium(Ii), Mercury(Ii), and Palladium(Ii), and Crystal Structure Analysis of Palladium Complex *Journal of the Chemical Society a—Inorganic Physical Theoretical*, 440-& (1971).

Filatov, M.A., Cheprakov, A.V., and Beletskaya, I.P. (2007), A facile and reliable method for the synthesis of tetrabenzoporphyrin from 4,7-dihydroisoindole. *European Journal of Organic Chemistry*, 3468-3475.

O. S. Finikova, A. V. Cheprakov, I. P. Beletskaya, P. J. Carroll and S. A. Vinogradov, Novel versatile synthesis of substituted tetrabenzoporphyrins, *J. Org. Chem.*, 2004, 69, 522-535.

M. A. Filatov, A. Y. Lebedev, S. A. Vinogradov and A. V. Cheprakov, *J. Org. Chem.*, 2008, 73, 4175-4185.

O. S. Finikova, S. E. Aleshchenkov, R. P. Briñas, A. V. Cheprakov, P. J. Carroll and S. A. Vinogradov, *J. Org. Chem.*, 2005, 70, 4617-4628.

* cited by examiner

2,2'-DISUBSTITUTED DIPYRRIN COMPOUNDS, SYNTHESIS THEREOF AND METHODS OF USE THEREOF

CROSS-REFERENCE TO RELATED APPLICATION

This application claims priority to U.S. Provisional Patent Application 61/250,201, filed Oct. 9, 2009, which is incorporated by reference herein in its entirety.

GOVERNMENT INTEREST

The work described herein was supported, in part, by National Institute of Health grant 10-03-01122a. The United States government may have certain rights in this application.

FIELD OF THE INVENTION

The present invention relates to 2,2'-di-substituted dipyrrins. The invention also relates to methods for the preparation of 2,2'-disubstituted dipyrrins, and to the use of 2,2'-disubstituted dipyrrins in, for example, sensing, imaging and laser applications.

BACKGROUND OF THE INVENTION

Boron dipyrromethenes, commonly known as BODIPY, form one of the most popular groups of organic flurophores, attracting interest from applications due to their high emission yields, photostability and versatile chemistry. The organic part of the BODIPY molecule is dipyrromethene (dipyrrin), which is responsible for the strongly allowed $\pi$-$\pi^*$ transition in the visible region of the spectrum. Coordination with boron rigidifies the dipyrrin skeleton, resulting in yet more intense absorption and bright fluorescence.

However, unlike BODIPY, the majority of metallodipyrrins do not fluoresce. Moreover, the interplay between the structure and the photophysical properties of metallodipyrrins has not yet been fully established, and overall metallodipyrrins are presently considered poorly emissive species.

The synthesis of dipyrrin compounds has been described, for example, by Maekawa et al., *Chemische Berichte*, 101, 847, 1968 and Shen et al., *Chemistry, A European Journal*, 10, 4853-4871, 2004. However, these processes suffer from certain drawbacks, such as lack of substitution capabilities, and/or low functional group tolerance.

Thus, there remains a need in the art for new highly emissive metallodipyrrin complexes that may be useful in, e.g., sensing, imaging and laser applications. Moreover, there also remains a need in the art for new processes for the synthesis of fluorogenic dipyrrin chelators that afford such compounds in improved yields and/or purities and is amenable to the introduction of a wide range of functional group substituents.

SUMMARY OF THE PRESENT INVENTION

In one embodiment, the present invention relates to a compound of Formula I:

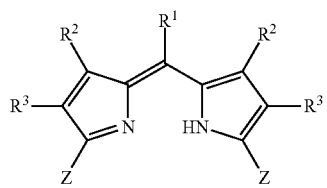

wherein
$R^1$ is H, alkyl, cycloalkyl, aryl or heteroaryl;
$R^2$ and $R^3$ are fused, in each case, to form a cycloalkenyl, aryl or heteroaryl group;
and Z is $CO_2R^x$, $C(O)R^x$, CN, $CON(R^x)_2$, $CS_2R^x$, $NO_2$, $PO_3(R^x)_2$, $S(O)R^x$ or $S(O)_2R^x$, wherein $R^x$ is, in each case, independently, H or alkyl;
with the proviso that said compound is not:
diethyl-7,7-difluoro-14-(1,4,7,10,13-pentaoxabenzoheptadecan-15-yl)-1,4,10,13-tetrahydro-1,4;10,13-bisethano-7-bora-7H-benzo[1,2-a;4,5-a']di-isoindole-5,9-dicarboxylate, or
diethyl-7,7-difluoro-14-(1,4,7,10,13-pentaoxabenzoheptadecan-15-yl)-7-bora-7H-benzo[1,2-a;4,5-a']diisoindole-5,9-dicarboxylate.

In another embodiment, the present invention relates to a metal complex of a compound of Formula I.

In another embodiment, the present invention relates to a process for preparing a compound of Formula I:

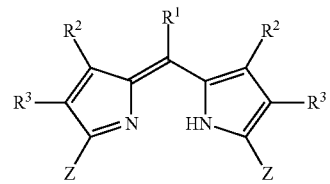

wherein
$R^1$ is H, alkyl, cycloalkyl, aryl or heteroaryl;
$R^2$ and $R^3$ are fused, in each case, to form a cycloalkenyl, aryl or heteroaryl group; and
Z is $CO_2R^x$, $C(O)R^x$, CN, $CON(R^x)_2$, $CS_2R^x$, $NO_2$, $PO_3(R^x)_2$, $S(O)R^x$ or $S(O)_2R^x$, wherein $R^x$ is, in each case independently, H or alkyl;
said process comprising:
(1) reacting a compound of formula (i) with a compound of formula (ii)

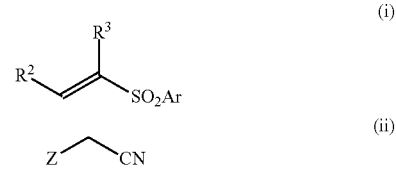

wherein Ar is formula (i) is aryl and Z in formula (ii) is —C(O)OR in which R is alkyl, aryl or alkylaryl;
to form a compound of formula (iii)

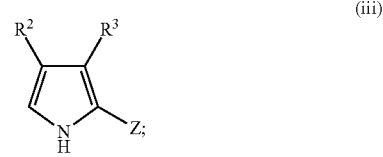

(2) reacting a compound of formula (iii) with either (a) $R^1$CHO, when $R^1$ in formula I is other than H, or (b) with $CH_2(OCH_3)_2$, when $R^1$ in formula I is H, to form a compound of formula (iv):

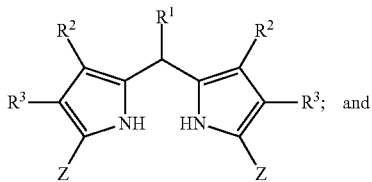

3) converting a compound of formula (iv) to a compound of Formula I.

In further embodiments, the present invention relates to various sensing, imaging and laser applications using compounds as described herein.

DETAILED DESCRIPTION OF THE PRESENT INVENTION

Figure 1:
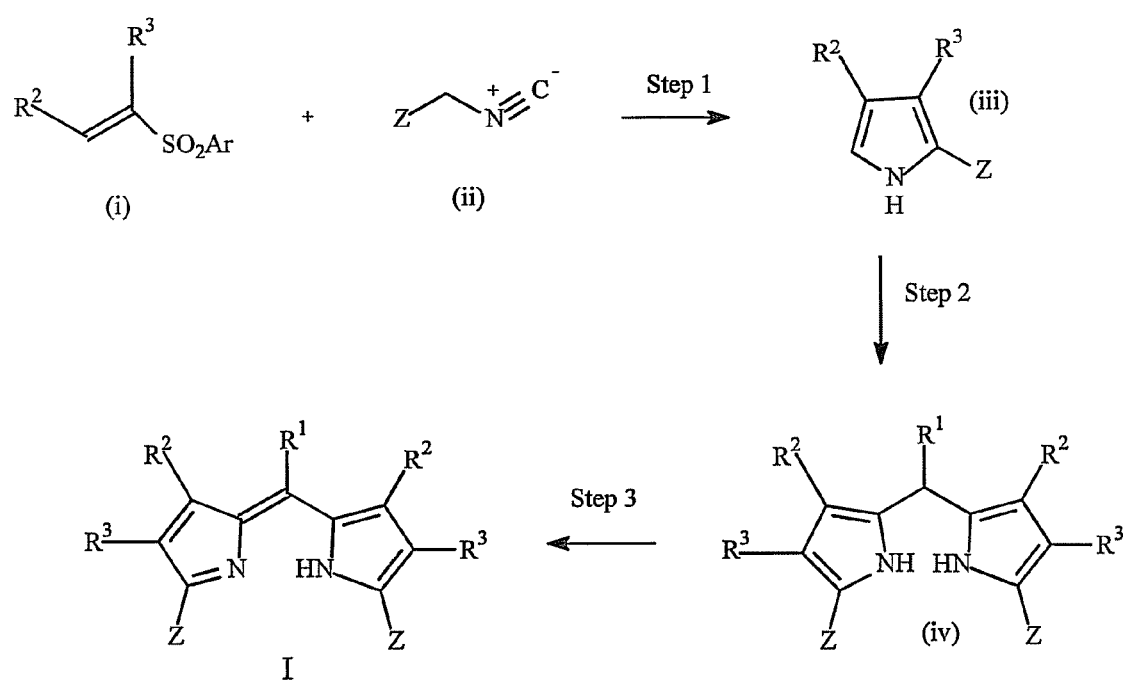
FIG. 1 depicts an exemplary synthesis of a compound of Formula I.

In one aspect, the present invention relates to compounds with tunable spectral properties, intrinsic sensitivity to metal ions and powerful fluorescence. The compounds are useful, for example, in sensing, imaging and laser applications.

Applicants have established that simple structural modifications of a dipyrrin molecule lead to dramatic enhancements in the ability of the compound to form fluorescent complexes with metal ions. In one embodiment, a relatively simple structural modification of the dipyrrin molecule that results in a dramatic enhancement of its ability to form fluorescent complexes with metal ions is described. In additional embodiments, the spectral properties of the new family of dipyrrins are tunable over the entire visible/near infrared range by way of, for example, annealing of the pyrrolic residues with external aromatic rings. Moreover, in further embodiments, the fluorescence of the metal chelates can be completely switched on and off upon changing the mode of the metal coordination.

In one aspect, this invention provides a compound of Formula I:

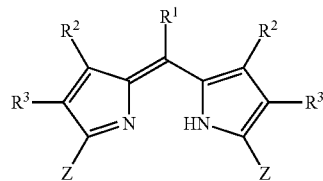

wherein $R^1$ is H, alkyl, cycloalkyl, aryl or heteroaryl;

$R^2$ and $R^3$ are fused, in each case, to form a cycloalkenyl, aryl or heteroaryl group; and Z is $CO_2R^x$, $C(O)R^x$, CN, $CON(R^x)_2$, $CS_2R^x$, $NO_2$, $PO_3(R^x)_2$, $S(O)R^x$ or $S(O)_2R^x$, wherein $R^x$ is, in each case, independently, H or alkyl;

with the proviso that said compound is not:

diethyl-7,7-difluoro-14-(1,4,7,10,13-pentaoxabenzoheptadecan-15-yl)-1,4,10,13-tetrahydro-1,4;10,13-bisethano-7-bora-7H-benzo[1,2-a;4,5-a']di-isoindole-5,9-dicarboxylate, or diethyl-7,7-difluoro-14-(1,4,7,10,13-pentaoxabenzoheptadecan-15-yl)-7-bora-7H-benzo[1,2-a;4,5-a']diisoindole-5,9-dicarboxylate.

In one embodiment, Z is $CO_2R^x$ or $C(O)R^x$. In embodiment, Z is $CO_2R^x$. In embodiment, Z is $C(O)R^x$ In one embodiment, $R^x$ is H. In one embodiment $R^x$ is alkyl ($R^x$ is methyl, ethyl). In one embodiment, Z is $CO_2CH_3$. In another embodiment, Z is $CO_2Et$. In another embodiment, Z is $CO_2H$. In one embodiment, a Z susbstituent enhances the chelating ability of a dipyrrin complex. In one embodiment, a Z susbstituent enhances the chelating ability of a dipyrrin complex with a metal ion.

In one embodiment, $R^1$ is H, aryl or heteroaryl. In one embodiment, $R^1$ is aryl or heteroaryl. In one embodiment $R^1$ is H or aryl. In another embodiment, $R^1$ is H. In another embodiment, $R^1$ is aryl. In another embodiment, $R^1$ is heteroaryl. For example, $R^1$ is aryl (e.g., phenyl) optionally substituted by hydroxyl, alkyl, carboxyalkyl, halogen and combinations thereof. For further example, $R^1$ is thienyl (e.g., 2-thienyl); halophenyl (e.g., bromophenyl, such as 4-bromophenyl), (carboxyalkyl)phenyl (e.g., (methoxycarbonyl) phenyl, such as 4-(methoxycarbonyl)phenyl); hydroxyphenyl (e.g., 2-hydroxyphenyl); or (dialkyl)phenyl (e.g., (di-t-butyl)phenyl, such as 3,5,-di-t-butyl-phenyl).

In one embodiment, $R^2$ and $R^3$ are fused to form a heteroaryl group. In one embodiment, $R^2$ and $R^3$ are fused to form a cyclalkenyl group. In one embodiment, $R^2$ and $R^3$ are fused to form a tetracyclohexeno group. In one embodiment, $R^2$ and $R^3$ are fused to form an aryl group. In one embodiment, $R^2$ and $R^3$ are fused to form a benzo group. In another embodiment, $R^2$ and $R^3$ are fused to form a naphtho group. In one embodiment, the naphtho group is attached to the nitrogen containing ring in a lateral mode.

For example, in additional embodiments, the compound of Formula I is represented by subformulas Ia-Ic:

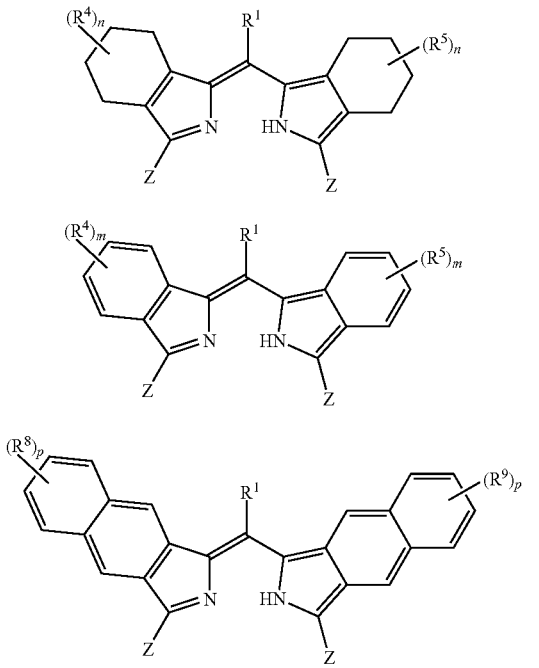

wherein
$R^4$, $R^5$, $R^6$, $R^7$, $R^8$ and $R^9$ are each, independently, hydrogen, halogen, hydroxyl, cyano, nitro, amino, alkylamino, dialkylamino, alkyl, alkenyl, alkynyl, cycloalkyl, aryl, alkylaryl, heteroaryl, alkylheteroaryl, heterocycle, alkylheterocycle, acyl, alkoxy, alkythio, arylthio, aminoalkyl, amidoalkyl, alkylsulfinyl, alkylsulfonyl, alkoxy, aryloxy or acyl, n is, in each case, 1, 2, 3, 4, 5, 6, 7 or 8;
m is, in each case, 1, 2, 3 or 4; and
p is, in each case, 1, 2, 3, 4, 5 or 6.

In one embodiment, $R^4$, $R^5$, $R^6$ and $R^7$ are each, independently, hydrogen, halogen, hydroxyl, cyano, nitro, amino, alkyl, cycloalkyl, aryl, alkylaryl, heteroaryl, alkylheteroaryl, heterocycle, alkylheterocycle or alkoxy.

In one embodiment, the compound of Formula I is represented by subformula Ia. In one embodiment, the compound of Formula I is represented by subformula Ib. In one embodiment, the compound of Formula I is represented by subformula Ic. In one embodiment, the compound of Formula I is represented by subformulas Ia and Ib.

In additional embodiments, the compound of Formula I is in the form of a metal complex. In certain embodiments, the metal complex is a boron, beryllium, magnesium, chromium, iron, nickel, copper, zinc, platinum, lithium, sodium, potassium, calcium, cadmium, silver, manganese, mercury, yttrium, lanthanum, gadolinium, scandium, ytterbium or lutetium complex.

In one embodiment, the metal complex is not a complex with boron. In one embodiment, the compound of Formula I is not a complex with a boron dihalide (e.g., boron difluoride).

In certain embodiments, the metal complex is a beryllium, magnesium, nickel, zinc, platinum, calcium, cadmium, mercury, yttrium, lanthanum, gadolinium, scandium, ytterbium or lutetium complex.

In certain embodiments, the metal complex is a nickel, zinc, lithium, sodium, potassium, calcium, cadmium, silver, manganese, mercury, yttrium, lanthanum, gadolinium, ytterbium or lutetium complex. In one embodiment, the metal complex is a zinc, calcium, cadmium, ytterbium, lanthanum, gadolinium or lutetium complex. In one embodiment, the metal complex is a calcium or zinc complex.

In certain embodiments, the compound of Formula I is a 1:1 complex with silver, lithium, sodium, potassium or mercury.

In other embodiments, the compound of Formula I is a 2:1 complex with calcium, zinc, cadmium or nickel. In other embodiments, the compound of Formula I is a 1:1 complex with calcium, zinc, cadmium or nickel.

In further embodiments, the compound of Formula I is a 3:1 complex with manganese, yttrium, lanthanum, gadolinium, ytterbium or lutetium.

Table 1 shows several exemplary metal salts that may be used to form metal complexes of Compounds of Formula I.

TABLE 1

Exemplary Metal Salts

| Metal Ion | Metal Salt | Metal Ion | Metal Salt |
|---|---|---|---|
| $Li^+$ | $LiOAc \times nH_2O$ | $Ni^{2+}$ | $Ni(OAc)_2 \times nH_2O$ |
| $Na^+$ | $NaOAc \times nH_2O$ | $Cd^{2+}$ | $Cd(OAc)_2 \times 2H_2O$ |
| $K^+$ | $KI$ | $Y^{3+}$ | $Y(OAc)_3 \times nH_2O$ |
| $Ag^+$ | $AgNO_3$ | $La^{3+}$ | $La(OAc)_3 \times nH_2O$ |
| $Hg^+$ | $HgCl$ | $Gd^{3+}$ | $Gd(NO_3)_3 \times nH_2O$ |
| $Ca^{2+}$ | $CaCl_2$ (anhydrous) | $Gd^{3+}$ | $GdCl_3 \times 6H_2O$ |
| $Zn^{2+}$ | $ZnBr_2$ (anhydrous) | $Yb^{3+}$ | $Yb(NO_3)_3 \times 5H_2O$ |
| $Mn^{2+}$ | $MnCl_2 \times 4H_2O$ | $Lu^{3+}$ | $LuCl_3 \times 6H_2O$ |

In certain embodiments, the compound of Formula I is selected from:
meso-(phenyl)-2,2'-diethoxycarbonyl-ditetracyclohexenodipyrrin (1);
meso-(4-methoxyphenyl)-2,2'-diethoxycarbonyl-ditetracyclohexenodipyrrin (2);
meso-(3,5-dimethoxycarbonylphenyl)-2,2'-diethoxycarbonyl-ditetracyclohexenodipyrrin (2a);
meso-(3,5-ditertbuthylpheny)-2,2'-diethoxycarbonyl-ditetracyclohexenodipyrrin (2b);
meso-(4-bromophenyl)-2,2'-diethoxycarbonyl-ditetracyclohexenodipyrrin (2c);
meso-(4-chloroophenyl)-2,2'-diethoxycarbonyl-ditetracyclohexenodipyrrin (2e);
meso-(4-methoxyphenyl)-2,2'-diethoxycarbonyl-ditetracyclohexenodipyrrin (2f);
2,2'-ditertbutoxycarbonyl-ditetracyclohexenodipyrrin (3);
meso-(phenyl)-2,2'-tertbutoxycarbonyl-ditetracyclohexenodipyrrin (4);
meso-(4-methoxycarbonylphenyl)-2,2'-tertbutoxycarbonyl-ditetracyclohexenodipyrrin (4a);
meso-(3,5-di-tertbutylphenyl)-2,2'-tertbutoxycarbonyl-ditetracyclohexenodipyrrin (4b);
meso-(4-bromophenyl)-2,2'-tertbutoxycarbonyl-ditetracyclohexenodipyrrin (4c);
meso-(4-chlorophenyl)-2,2'-tertbutoxycarbonyl-ditetracyclohexenodipyrrin (4d);
meso-(4-methoxycarbonylphenyl)-2,2'-diethoxycarbonyl-di(dihydroxytetracyclohexeno)dipyrrin (5);
2,2'-diethoxycarbonyl-dibenzodipyrrin (6);
meso-(phenyl)-2,2'-diethoxycarbonyl-dibenzodipyrrin (7);
meso-(4-methoxycarbonylphenyl)-2,2'-diethoxycarbonyl-dibenzodipyrrin (7a);

meso-(3,5-dimethoxycarbonylphenyl)-2,2'-diethoxycarbonyl-dibenzodipyrrin (7b);
meso-(3,5-ditertbutylphenyl)-2,2'-diethoxycarbonyl-dibenzodipyrrin (7c);
meso-(4-bromophenyl)-2,2'-diethoxycarbonyl-dibenzodipyrrin (7d);
meso-(4-chlorophenyl)-2,2'-diethoxycarbonyl-dibenzodipyrrin (7e);
meso-(4-methoxyphenyl)-2,2'-diethoxycarbonyl-dibenzodipyrrin (7f);
2,2'-tertbutoxycarbonyl-dibenzodipyrrin (8);
meso-(phenyl)-2,2'-tertbutoxycarbonyl-dibenzodipyrrin (9);
meso-(4-methoxycarbonylphenyl)-2,2'-tertbutoxycarbonyl-dibenzodipyrrin (9a);
meso-(3,5-ditertbutylphenyl)-2,2'-tertbutoxycarbonyl-dibenzodipyrrin (9b);
meso-(4-bromophenyl)-2,2'-tertbutoxycarbonyl-dibenzodipyrrin (9c);
meso-(4-chlorophenyl)-2,2'-tertbutoxycarbonyl-dibenzodipyrrin (9d);
2,2'-diethoxycarbonyl-dinaphthodipyrrin (10);
meso-(phenyl)-2,2'-diethoxycarbonyl-dinaphthodipyrrin (11);
meso-(4-methoxycarbonylphenyl)-2,2'-diethoxycarbonyl-dinaphthodipyrrin (11a);
meso-(3,5-dimethoxycarbonylphenyl)-2,2'-diethoxycarbonyl-dinaphthodipyrrin (11b);
meso-(3,5-ditertbutylphenyl)-2,2'-diethoxycarbonyl-dinaphthodipyrrin (11c);
meso-(4-bromophenyl)-2,2'-diethoxycarbonyl-dinaphthodipyrrin (11d);
meso-(4-chlorophenyl)-2,2'-diethoxycarbonyl-dinaphthodipyrrin (11e);
meso-(4-methoxyphenyl)-2,2'-diethoxycarbonyl-dinaphthodipyrrin (11f);
2,2'- tertbutoxycarbonyl-dinaphthodipyrrin (12);
meso-(phenyl)-2,2'-tertbutoxycarbonyl-dinaphthodipyrrin (13);
meso-(4-methoxycarbonylphenyl)-2,2'-tertbutoxycarbonyl-dinaphthodipyrrin (13a);
meso-(3,5-ditertbutylphenyl)-2,2'-tertbutoxycarbonyl-dinaphthodipyrrin (13b);
meso-(4-bromophenyl)-2,2'-tertbutoxycarbonyl-dinaphthodipyrrin (13c); and
meso-(4-chlorophenyl)-2,2'-tertbutoxycarbonyl-dinaphthodipyrrin (13d).

In additional embodiments, the compound of Formula I is in the form of a metal complex of any of compounds (1)-(13d).

In additional embodiments, the compound of Formula I is in the form of a zinc, cadmium or calcium complex of any of compounds (1)-(13d).

In additional embodiments, the compound of Formula I is in the form of a lanthanum, yttrium, gadolinium, ytterbium, lutetium or copper complex of any of compounds (6), (7a), (9a), (9b), (12) and (13b).

In certain embodiments, the compound of Formula I is selected from:
2,2'-diethoxycarbonyl-dibenzodipyrrin (6);
meso-(phenyl)-2,2'-diethoxycarbonyl-dibenzodipyrrin (7);
meso-(4-methoxycarbonylphenyl)-2,2'-diethoxycarbonyl-dibenzodipyrrin (7a);
meso-(3,5-dimethoxycarbonylphenyl)-2,2'-diethoxycarbonyl-dibenzodipyrrin (7b);
meso-(3,5-ditertbutylphenyl)-2,2'-diethoxycarbonyl-dibenzodipyrrin (7c);
meso-(4-bromophenyl)-2,2'-diethoxycarbonyl-dibenzodipyrrin (7d);
meso-(4-chlorophenyl)-2,2'-diethoxycarbonyl-dibenzodipyrrin (7e);
meso-(4-methoxyphenyl)-2,2'-diethoxycarbonyl-dibenzodipyrrin (7f);
2,2'-tertbutoxycarbonyl-dibenzodipyrrin (8);
meso-(phenyl)-2,2'-tertbutoxycarbonyl-dibenzodipyrrin (9);
meso-(4-methoxycarbonylphenyl)-2,2'-tertbutoxycarbonyl-dibenzodipyrrin (9a);
meso-(3,5-ditertbutylphenyl)-2,2'-tertbutoxycarbonyl-dibenzodipyrrin (9b);
meso-(4-bromophenyl)-2,2'-tertbutoxycarbonyl-dibenzodipyrrin (9c);
meso-(4-chlorophenyl)-2,2'-tertbutoxycarbonyl-dibenzodipyrrin (9d);
2,2'-diethoxycarbonyl-dinaphthodipyrrin (10);
meso-(phenyl)-2,2'-diethoxycarbonyl-dinaphthodipyrrin (11);
meso-(4-methoxycarbonylphenyl)-2,2'-diethoxycarbonyl-dinaphthodipyrrin (11a);
meso-(3,5-dimethoxycarbonylphenyl)-2,2'-diethoxycarbonyl-dinaphthodipyrrin (11b);
meso-(3,5-ditertbutylphenyl)-2,2'-diethoxycarbonyl-dinaphthodipyrrin (11c);
meso-(4-bromophenyl)-2,2'-diethoxycarbonyl-dinaphthodipyrrin (11d);
meso-(4-chlorophenyl)-2,2'-diethoxycarbonyl-dinaphthodipyrrin (11e);
meso-(4-methoxyphenyl)-2,2'-diethoxycarbonyl-dinaphthodipyrrin (11f);
2,2'-tertbutoxycarbonyl-dinaphthodipyrrin (12);
meso-(phenyl)-2,2'-tertbutoxycarbonyl-dinaphthodipyrrin (13);
meso-(4-methoxycarbonylphenyl)-2,2'-tertbutoxycarbonyl-dinaphthodipyrrin (13a);
meso-(3,5-ditertbutylphenyl)-2,2'-tertbutoxycarbonyl-dinaphthodipyrrin (13b);
meso-(4-bromophenyl)-2,2'-tertbutoxycarbonyl-dinaphthodipyrrin (13c); and
meso-(4-chlorophenyl)-2,2'-tertbutoxycarbonyl-dinaphthodipyrrin (13d).

In additional embodiments, the compound of Formula I is in the form of a metal complex of any of compounds (6)-(13d).

In additional embodiments, the compound of Formula I is in the form of a zinc, cadmium or calcium complex of any of compounds (6)-(13d).

In additional embodiments, the compound of Formula I is in the form of a lanthanum, yttrium, gadolinium, ytterbium, lutetium or copper complex of any of compounds (6), (7a), (9a), (9b), (12) and (13b).

Synthesis of 2,2'-Disubstituted Dipyrrins.

In another aspect, the present invention relates to novel methods for the preparation of 2,2'-disubstituted dipyrrins (DPMs). In certain embodiments, the synthetic methods disclosed herein provide 2,2'-disubstituted dipyrrins in improved yields and/or improved purities. In further embodiments, the methods also allow for facile introduction of a variety of useful functional groups into a DPM molecule, thus allowing the properties (e.g., solubility, functionalizaion) of a DPM molecule to be tailored to suit a particular application.

In one embodiment, this invention provides a process for preparing a compound of Formula I:

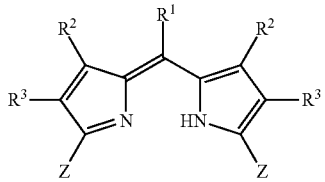

wherein
$R^1$ is H, alkyl, cycloalkyl, aryl or heteroaryl;
$R^2$ and $R^3$ are fused, in each case, to form a cycloalkenyl, aryl or heteroaryl group; and
Z is $CO_2R^x$, $C(O)R^x$, CN, $CON(R^x)_2$, $CS_2R^x$, $NO_2$, $PO_3(R^x)_2$, $S(O)R^x$ or $S(O)_2R^x$, wherein $R^x$ is, in each case independently, H or alkyl;
said process comprising:
(1) reacting a compound of formula (i) with a compound of formula (ii)

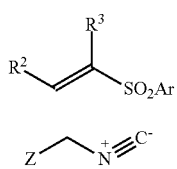

wherein Ar is formula (i) is aryl and Z in formula (ii) is —C(O)OR in which R is alkyl (e.g., methyl, ethyl, tert-butyl), aryl or alkylaryl (e.g., benzyl);
to form a compound of formula (iii)

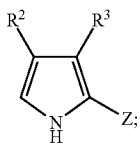

(2) reacting a compound of formula (iii) with either (a) $R^1CHO$, when $R^1$ in formula I is other than H, or (b) with $CH_2(OCH_3)_2$, when $R^1$ in formula I is H, to form a compound of formula (iv):

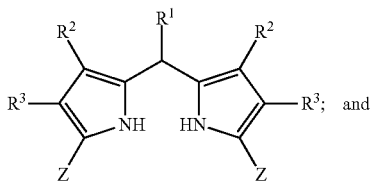

3) converting a compound of formula (iv) to a compound of Formula I.
In one embodiment, an exemplary synthetic process as described herein is shown in FIG. 1.
In one embodiment, Z is $CO_2R^x$ or $C(O)R^x$. In embodiment, Z is $CO_2R^x$. In embodiment, Z is $C(O)R^x$ In one embodiment, $R^x$ is H. In one embodiment $R^x$ is alkyl ($R^x$ is methyl, ethyl). In one embodiment, Z is $CO_2CH_3$. In another embodiment, Z is $CO_2Et$. In another embodiment, Z is $CO_2H$.
In one embodiment, $R^1$ is H, aryl or heteroaryl. In one embodiment, $R^1$ is aryl or heteroaryl. In one embodiment $R^1$ is H or aryl. In another embodiment, $R^1$ is H. In another embodiment, $R^1$ is aryl. In another embodiment, $R^1$ is heteroaryl. For example, $R^1$ is aryl (e.g., phenyl) optionally substituted by hydroxyl, alkyl, carboxyalkyl, halogen and combinations thereof. For further example, $R^1$ is thienyl (e.g., 2-thienyl); halophenyl (e.g., bromophenyl, such as 4-bromophenyl), (carboxyalkyl)phenyl (e.g., (methoxycarbonyl)phenyl, such as 4-(methoxycarbonyl)phenyl); hydroxyphenyl (e.g., 2-hydroxyphenyl); or (dialkyl)phenyl (e.g., (di-t-butyl)phenyl, such as 3,5,-di-t-butyl-phenyl).
In one embodiment, $R^2$ and $R^3$ are fused to form a heteroaryl group. In one embodiment, $R^2$ and $R^3$ are fused to form a cyclalkenyl group. In one embodiment, $R^2$ and $R^3$ are fused to form a tetracyclohexeno group. In one embodiment, $R^2$ and $R^3$ are fused to form an aryl group. In one embodiment, $R^2$ and $R^3$ are fused to form a benzo group. In another embodiment, $R^2$ and $R^3$ are fused to form a naphtho group. In one embodiment, the naphtho group is attached to the nitrogen containing ring in a lateral mode.
In certain embodiments, step (1) is conducted in a solvent, such as, but not limited to, THF, dioxane, diethyl ether, and the like. In one embodiment, step (1) is conducted in THF.
In certain embodiments, step (1) is conducted in the presence a base, such as, but not limited to, metal alkoxides (e.g., t-BuOK), lithium diisopropylamide, sodium silazide, and the like. In one embodiment, step (1) is conducted in the presence of t-BuOK.
In certain embodiments, step (2) is conducted in a solvent such as, but not limited to, methylene chloride, chloroform, tetrachloroethane, carbon tetrachloride, and the like. In one embodiment, step (2) is conducted in methylene chloride.
In certain embodiments, step (2) is conducted in the presence of an acid such as, but not limited to, p-toluenesulfonic acid (PTSA), acetic acid, trifluoroacetic acid, propionic acid, and the like. In one embodiment, step (2) is conducted in the presence of p-toluenesulfonic acid.
In certain embodiments, step (2) is conducted in the presence of an ammonium halide salt, such as, but not limited to, tetra-n-butyl-ammonium chloride, tetra-n-butyl-ammonium bromide, and the like. In one embodiment, step (2) is conducted in the presence of tetra-n-butyl-ammonium chloride. In certain embodiments, Applicants have surprisingly found that conducing step (2) in the presence of an ammonium halide salt, such as tetra-n-butyl-ammonium chloride, reduces detrimental side reactions from occurring and also reduces tarring, thereby providing for a product with improved yield and purity.
In certain embodiments, step (3) is conducted in a solvent such as, but not limited to, THF, $CH_2Cl_2$, $CHCl_3$, $CCl_4$, toluene, and the like. In one embodiment, step (3) is conducted in THF.
In certain embodiments, step (3) is conducted in the presence of an oxidizing agent, such as, but not limited to, 2,3-dichloro-5,6-dicyanobenzoquinone (DDQ), tetrachloro-1,4,-benzoiquinone (p-chloranil). In one embodiment, step (3) is conducted in the presence of 2,3-dichloro-5,6-dicyanobenzoquinone.
In one embodiment, step (2) is conducted without isolating the product of step (1).
In one embodiment, step (3) is conducted without isolating the product of step (2).

In another embodiment, steps (1), (2) and (3) and conducted in situ, without isolating any intermediate products.

In one embodiment, the synthetic processes described herein further comprise step (4): converting a compound of Fomula I to a metal complex of a compound of Formula I. In one embodiment, step (4) comprises contacting a compound of Formula I with a metal salt.

In certain embodiments, step (4) comprises reacting a compound of Formula I with a metal salt wherein said metal salt is a boron, beryllium, magnesium, chromium, iron, nickel, copper, zinc, platinum, lithium, sodium, potassium, calcium, cadmium, silver, manganese, mercury, yttrium, lanthanum, gadolinium, scandium, ytterbium or lutetium salt. In one embodiment, step (4) comprises reacting a compound of Formula I with a metal salt wherein said metal salt is a zinc, calcium, cadmium, ytterbium, lanthanum, gadolinium or lutetium salt. In one embodiment, step (4) comprises reacting a compound of Formula I with a metal salt wherein said metal salt is a calcium or zinc salt.

In certain embodiments, the metal salt is selected from acetate salts (e.g., $Ni(OAc)_2$, $Cd(OAc)_2$, $Y(OAc)_3$, $La(OAc)_3$, LiOAc, NaOAc); nitrite salts (e.g., $Gd(NO_3)_3$, $Y(NO_3)_3$, $Yb(NO_3)_3$, $AgNO_3$); and halide salts (e.g., HgCl, $CaCl_2$, $ZnBr_2$, $MnCl_2$, KI, $GdCl_3$, $LuCl_3$). In certain embodiments, the metal salt is anhydrous (e.g., anhydrous $CaCl_2$, anhydrous $ZnBr_2$). In certain embodiments, the metal salt is a hydrate (e.g., $Ni(OAc)_2 \cdot (H_2O)_n$, $Cd(OAc)_2 \cdot (H_2O)_2$, $Y(OAc)_3 \cdot (H_2O)_n$, $La(OAc)_3 \cdot (H_2O)_n$, $LiOAc \cdot (H_2O)_n$, $NaOAc \cdot (H_2O)_n$, $Gd(NO_3)_3 \cdot (H_2O)_n$, $Y(NO_3)_3 \cdot (H_2O)_n$, $Yb(NO_3)_3 \cdot (H_2O)_5$, $GdCl_3 \cdot (H_2O)_6$, $LuCl_3 \cdot (H_2O)_6$, $MnCl_2 \cdot (H_2O)_4$). In one embodiment, n is 6.

In additional embodiments of any of the processes described herein, the compound of Formula I is not diethyl-7,7-difluoro-14-(1,4,7,10,13-pentaoxabenzoheptadecan-15-yl)-1,4,10,13-tetrahydro-1,4;10,13-bisethano-7-bora-7H-benzo[1,2-a;4,5-a']di-isoindole-5,9-dicarboxylate or diethyl-7,7-difluoro-14-(1,4,7,10,13-pentaoxabenzoheptadecan-15-yl)-7-bora-7H-benzo[1,2-a;4,5-a']diisoindole-5,9-dicarboxylate.

In additional embodiments of any of the processes described herein, step (4) does not involve forming a complex with boron. For example, step (4) does not involve forming a complex with a boron dihalide (e.g., boron difluoride).

In certain embodiments, step (4) is conducted in a solvent such as, but not limited to, dimethylformamide (DMF), THF, acetone, methanol, toluene, benzonitrile, DCM, and the like. In one embodiments, step (4) is conducted in acetone.

In additional embodiments, a process as described herein may be used to prepare any of compounds (1)-(13d).

In additional embodiments, a process as described herein may be used to prepare a metal complex of any of compounds (1)-(13d).

In additional embodiments, a process as described herein may be used to prepare a zinc, cadmium or calcium complex of any of compounds (1)-(13d).

In additional embodiments, a process as described herein may be used to prepare a lanthanum, yttrium, gadolinium, ytterbium, lutetium or copper complex of any of compounds (6), (7a), (9a), (9b), (12) and (13b).

Optical Properties of 2,2'-Disubstituted Dipyrrin Compounds

The 2,2'-disubstituted dipyrrin (DPM) compounds of the present invention readily form complexes with metal ions. In contrast, metallation of DPMs without 2,2'-substitutents typically requires heating and/or the presence of bases, and typically results in non-emissive products.

Applicants have surprisingly found that upon formation of a metal complex, the color of a solution a 2,2'-disubstituted dipyrrin compound of the present invention undergoes a dramatic change. For example, in certain embodiments, in the case of complexation of $Zn^{2+}$ or $Ca^{2+}$ by a 2,2'-diethoxycarbonyl substituted dipyrrins, the color of a solution immediately changes from purple to deep-blue. In different embodiments, the complex-forming ability of a 2,2'-disubstituted dipyrrin compound as described herein varies with the ligand and the solvent used. Typically, in certain embodiments, the complexes exhibit extremely high stability constants, in particular, complexes formed with, for example, calcium or zinc. As a result, in further embodiments, the presence of even trace amount of metal ions leads to a drastic change in the solution color.

Figure 2:
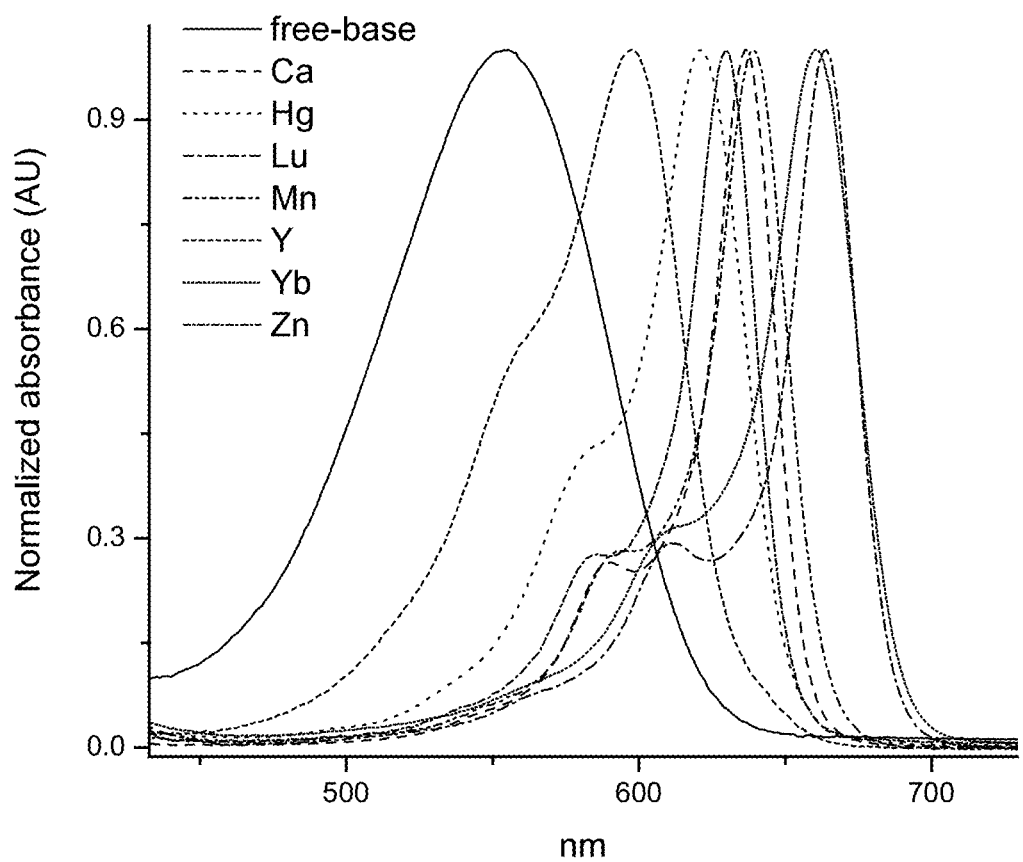
FIG. 2 depicts normalized absorption spectra of 2,2'-diethoxycarbonyl-dibenzopyrromethene and some of its metal complexes in DMF.

FIG. 2 shows the absorption spectra of Zn 2,2'-diethoxycarbonyl-dibenzodipyrrin and several of its metal complexes in DMF. Typically, the absorption spectra of the metal complexes reveal narrow absorption bands, accompanied by characteristic short-wavelength shoulders. The absorption and emission bands of 2,2'-disubstituted dipyrrin metal complexes of the present invention span the whole visible/near infrared spectrum. In contrast, the absorption spectrum of non metal-complexed dipyrrin ligands are relatively broad and featureless. In certain embodiments, the extinction coefficients of the metal complexes are in the range of about $5 \times 10^4$ to about $10^5$ $M^{-1} cm^{-1}$. In cetain embodiments, the extinction coefficicient is comparable to the extinction of rhodamines and fluoresceines.

Figure 3:
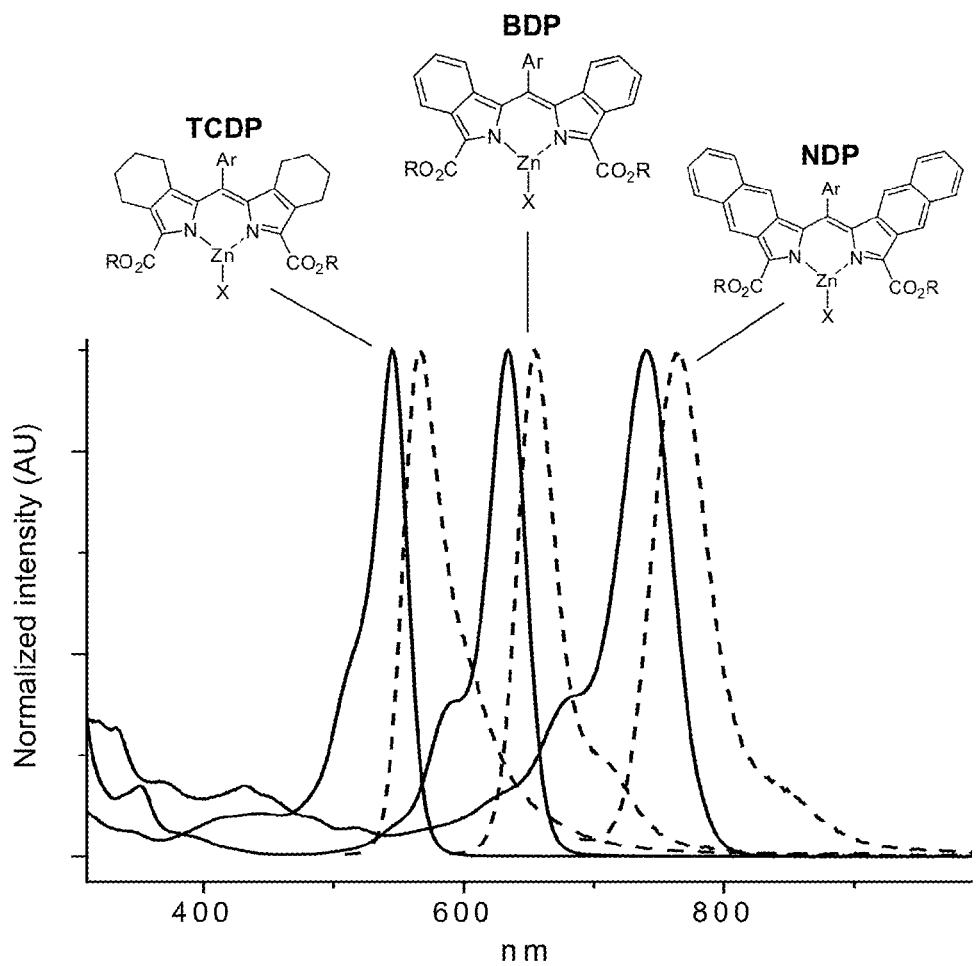
FIG. 3 depicts absorption spectra of zinc complexes of meso-aryl-2,2'-dialkoxycarbonyl-ditetracyclohexenodipyrrin (TCDP), meso-aryl-2,2'-dialkoxycarbonyl-dibenzodipyrrin (BDP) and meso-aryl-2,2'-dialkoxycarbonyl-dinaphthodipyrrin (NDP) in DMF.

FIG. 3 shows the absorption spectra in DMF for Zn meso-4-(methoxycarbonyl)phenyl-2,2'-ditertbutoxycarbonyl-ditetracyclohexenodipyrrin, Zn meso-4-(methoxycarbonyl)phenyl-2,2'-ditertbutoxycarbonyl-dibenzodipyrrin and Zn meso-4-(methoxycarbonyl)phenyl-2,2'-diethoxycarbonyl-dinaphthodipyrrin. As can be seen, an increase in the size of the π-extended aromatic system of the ligand leads to a progressive red-shift in the absorption spectra: ($\lambda_{max}$(TCDP)< $\lambda_{max}$(BDP)<$\lambda_{max}$(NDP). The fluorescence spectra (see Table 3, below) follow the same trend. Therefore, in further embodiments, changing the degree of π-conjugation of the dipyrrin compound, which is easily attainable through the use of the synthetic methods described herein, allows for tuning of the optical transition of DPM-based chromophores, thus allowing a compound to be tailored to a particular application, if desired.

Figure 4:
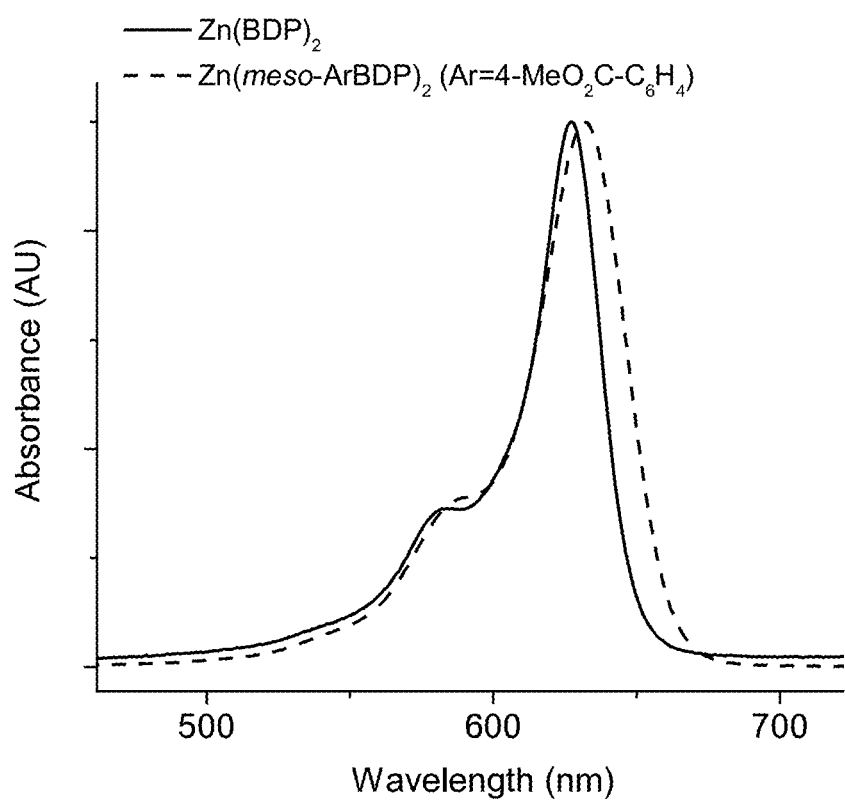
FIG. 4 depicts the absorption spectra of zinc complexes of 2,2'-diethoxycarbonyl dibenzopyrromethene and meso-Ar-2, 2'-diethoxycarbonyldibenzopyrromethene (Ar=4-MeO$_2$C—C$_6$H$_4$) in DMF.

FIG. 4 shows the absorption spectra in DMF of Zn 2,2'-ditertbutoxycarbonyl-dibenzodipyrrin and Zn meso-4-(methoxycarbonyl)phenyl-2,2'- ditertbutoxycarbonyl-dibenzodipyrrin. Typically meso Ar substituted BDP's exhibit very small spectral red-shifts compared to their meso-unsubstituted analogs. However, applicants have found that meso-Ar substituted DPM's also form brightly colored complexes with metal ions. As described above, the synthesis of meso-aryl substited DPM's involves condensation with an aromatic aldehyde, which serves as the source of the meso-aryl group. Since aromatic aldehydes with different functionalities are readily commercially available, in certain embodiments, DPM's with a wide range of functional groups, suitable for further derivatization, are easily obtainable by the synthetic methods disclosed herein.

Figure 5:
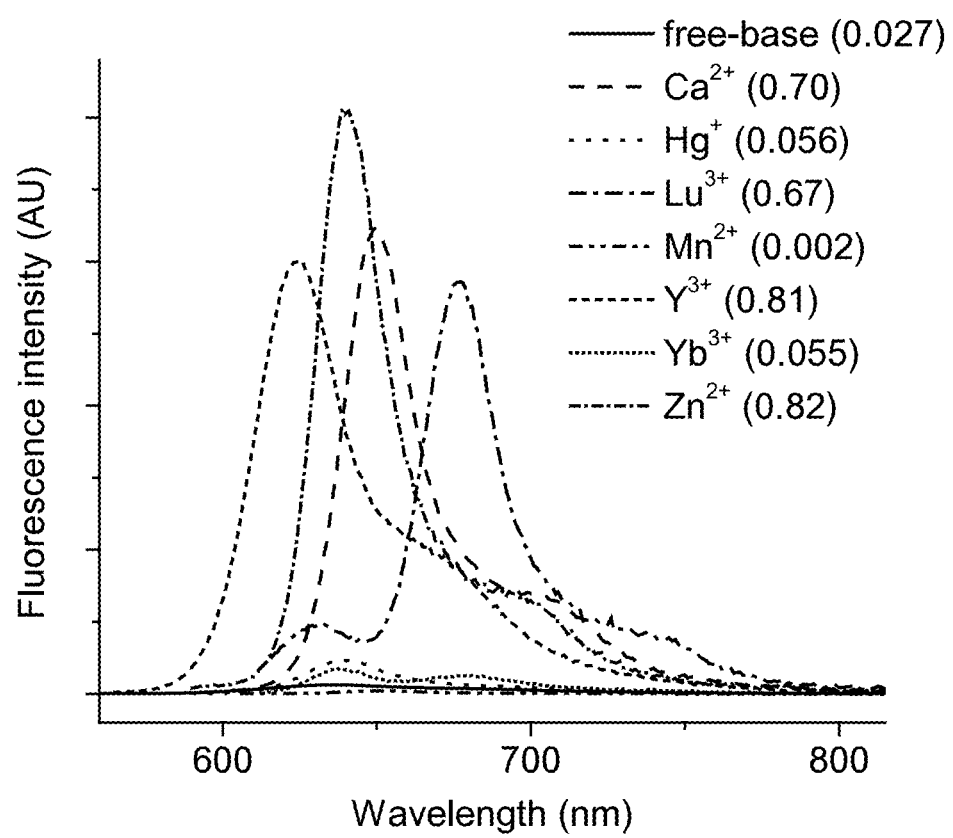
FIG. 5 depicts fluorescence spectra of 2,2'-diethoxycarbonyldibenzopyrromethene and its metal complexes in DMF. The plots are scaled to reflect the fluorescence quantum yields (shown in parentheses).

The free-base dipyrrins and meso-aryl-dipyrrins of the present invention exhibit broad featureless absorption spectra and fluorescence only weakly ($\phi_{fl}$~0.01-0.02). Upon treatment with organic bases (such as $Et_3N$, DBU etc.), dipyrrins (including their meso-arylated derivatives) easily form anions, whose spectra are red-shifted compared to those of the respective free-bases. These anions also fluoresce very weakly ($\phi_{fl}$~0.01-0.02). However, Applicants have discovered that metal complexes of 2,2'-disubstituted dipyrrins, as described herein, exhibit extremely bright fluorescence, which in most cases can be readily detected by the naked eye. FIG. 5 shows the fluorescence spectra for Zn meso-4-(methoxycarbonyl)phenyl-2,2'-ditertbutoxycarbonyl-dibenzodipyrrin and several metals salts thereof. Table 3 gives optical properties of several metal complexes of 2,2'-diethoxycarbonyl-dibenzopyrromethenes described herein.

TABLE 3

Optical properties of in situ prepared metal complexes of 2,2'-diethoxycarbonyl-dibenzopyrromethenes in DMF.

| Metal ion | Abs $\lambda_{max}$, nm | Emiss $\lambda_{max}$, nm | $\phi_{fl}^{[a]}$ | Metal ion | Abs $\lambda_{max}$, nm | Emiss $\lambda_{max}$, nm | $\phi_{fl}^{[a]}$ |
|---|---|---|---|---|---|---|---|
| Compound 6 | | | | Compound 6 | | | |
| $Zn^{2+}$ | 637 | 650 | 0.67 | $Y^{3+}$ | 598 | 626 | 0.75 |
| $Ca^{2+}$ | 639 | 650 | 0.64 | $La^{3+}$ | 650 | 667 | 0.49 |
| $Cd^{2+}$ | 636 | 650 | 0.64 | $Gd^{3+}$ | 657 | 675 | 0.37 |
| $Hg^{2+}$ | 621 | 641 | 0.05 | $Yb^{3+}$ | 661 | 639 | 0.07 |
| Compound 9a | | | | Compound 9a | | | |
| $Zn^{2+}$ | 631 | 639 | 0.65 | $Cd^{2+}$ | 632 | 641 | 0.51 |
| $Ca^{2+}$ | 638 | 645 | 0.58 | $Yb^{3+}$ | 664 | 673 | $0.02^{[b]}$ |
| Compound 11a | | | | Compound 11a | | | |
| $Zn^{2+}$ | 740 | 761 | 0.08 | $Ca^{2+}$ | 737 | 762 | 0.05 |

$^{[a]}$relative to rhodamine 6G in EtOH ($\phi_{fl}$ = 0.94);
$^{[b]}$in acetone.

As can be seen from Table 3, the fluorescence quantum yields vary between the metal complexes. In certain embodiments, the quantum yield is between about 0.1 and about 0.8. In certain embodiments, the quantum yield is highest, for example, for $Zn^{2+}$, $Ca^{2+}$, $Cd^{2+}$, $Y^{3+}$, $La^{3+}$, $Gd^{3+}$, $Lu^{3+}$ complexes.

Moreover, Applicants have surprisingly found that the fluoresence properties of a metal complex can be altered (e.g., "switched on" or "switched off") by altering the mode of metal coordination.

In certain embodiments, the 2,2'-disubstituted DPM ligands (L) described herein are in the form of a mono complex (ML) with a metal M. In certain embodiments, the 2,2'-disubstituted DPM ligands (L) described herein are in the form of a bis complex ($ML_2$) with a metal M. In certain embodiments, the 2,2'-disubstituted DPM ligands (L) described herein are in equilibrium between mono (ML) and bis ($ML_2$) forms (M=metal, e.g., zinc, calcium).

In certain embodiments, the bis complex ($ML_2$) complex form precipitates from solution.

In certain embodiments, the bis-($ML_2$) complex form exhibits little or no fluorescence. In other embodiments, the mono (ML) complex form exhibits strong fluorescence.

In certain embodiments, spectral transision of 2,2' disubstituted compounds described herein can be tuned into a desired range. For example, in certin embodiments, spectral transision of 2,2' disubstituted compounds described herein can be tuned into a desired range by varying the degree of π-conjugation. In certain embodiments, spectral transision of 2,2' disubstituted compounds described herein can be tuned without altering the chelating ability of the compound.

Without wishing to be bound by theory, Applicants believe that the high lability of 2,2'-dialkoxycarbonyl substituted DPMs may be a result of destabilization due to steric strain induced by the 2,2' substituents and the electron withdrawing effects of these substituents. When positioned in close proximity to chelating nitrogen atoms, the carbonyl groups may decrease the basicity of the ligand and fascilitate exchange reactions.

Morever, and also without wishing to be bound by theory Applicants believe that the difference in fluorescence and lack of fluorescence of the $ML_2$ complexes is due to an exciton coupling effect. In one embodiment, mono- ML complexes are fluorescent, bis $ML_2$ complexes are not fluorescent.

Methods of Use/Applications

As described above, the 2,2'-disubstituted dipyrrins described herein undergo dramatic color changes upon complexation with metal ions. Thus, these compounds can readily be used in a variety of, for example, sensing, imaging and laser applications. In one embodiment, the compound is used in a sensing application. In one embodiment, the compound is used in an imagaing application. In one embodiment, the compound is used in a laser application.

Thus, in another aspect, the present invention relates to a colorimetric detector (e.g., for a metal ion) comprising a compound of Formula I:

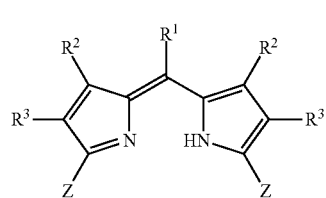

I wherein
$R^1$ is H, alkyl, cycloalkyl, aryl or heteroaryl;
$R^2$ and $R^3$ are fused, in each case, to form a cycloalkenyl, aryl or heteroaryl group; and
Z is $CO_2R^x$, $C(O)R^x$, CN, $CON(R^x)_2$, $CS_2R^x$, $NO_2$, $PO_3(R^x)_2$, $S(O)R^x$ or $S(O)_2R^x$, wherein $R^x$ is, in each case independently, H or alkyl.

In one embodiment, Z is $CO_2R^x$ or $C(O)R^x$. In embodiment, Z is $CO_2R^x$. In embodiment, Z is $C(O)R^x$ In one embodiment, $R^x$ is H. In one embodiment $R^x$ is alkyl ($R^x$ is methyl, ethyl). In one embodiment, Z is $CO_2CH_3$. In another embodiment, Z is $CO_2Et$. In another embodiment, Z is $CO_2H$.

In one embodiment, $R^1$ is H, aryl or heteroaryl. In one embodiment, $R^1$ is aryl or heteroaryl. In one embodiment $R^1$ is H or aryl. In another embodiment, $R^1$ is H. In another embodiment, $R^1$ is aryl. In another embodiment, $R^1$ is heteroaryl. For example, $R^1$ is aryl (e.g., phenyl) optionally substituted by hydroxyl, alkyl, carboxyalkyl, halogen and combinations thereof. For further example, $R^1$ is thienyl (e.g., 2-thienyl); halophenyl (e.g., bromophenyl, such as 4-bromophenyl), (carboxyalkyl)phenyl (e.g., (methoxycarbonyl)phenyl, such as 4-(methoxycarbonyl)phenyl); hydroxyphenyl (e.g., 2-hydroxyphenyl); or (dialkyl)phenyl (e.g., (di-t-butyl)phenyl, such as 3,5,-di-t-butyl-phenyl).

In one embodiment, $R^2$ and $R^3$ are fused to form a heteroaryl group. In one embodiment, $R^2$ and $R^3$ are fused to form a cyclalkenyl group. In one embodiment, $R^2$ and $R^3$ are fused to form a tetracyclohexeno group. In one embodiment, $R^2$ and $R^3$ are fused to form an aryl group. In one embodiment, $R^2$ and $R^3$ are fused to form a benzo group. In another embodiment, $R^2$ and $R^3$ are fused to form a naphtho group. In one embodiment, the naphtho group is attached to the nitrogen containing ring in a lateral mode.

In one embodiment, the colorimetric detector exhibits a color change upon contact (e.g., binding) with a metal ion.

In a further aspect, the present invention relates to a method for detecting a metal ion comprising (i) exposing a sample to a compound of Formula I, and (ii) determining a change in color of said sample resulting from exposure to a compound of Formula I.

In a further aspect, the present invention relates to a method for detecting a metal ion comprising (i) exposing a sample to a compound of Formula I, wherein said exposure results in a change in color of the sample, and (ii) detecting said change in color of said sample.

As discussed above, 2,2'-disubstituted dipyrrins display extremely bright fluorescence. Thus, in certain embodiments, 2,2'-disubstituted dipyrrin metal complexes, e.g., complexes with zinc, calcium, cadmium, yttrium, lanthanum, gadolinium and/or lutetium (e.g., complexes with $Zn^{2+}$, $Ca^{2+}$, $Cd^{2+}$, $Y^{3+}$, $La^{3+}$, $Gd^{3+}$ or $Lu^{3+}$ compounds) can be used as highly efficient fluorescent markers and probes. In addition, in further embodiments, free base 2,2'-disubstituted dipyrrins can be considered as analytical fluorescent reagents for metal ions, e.g., in certain embodiments as analytical fluorescent reagents for zinc, calcium, cadmium, yttrium, lanthanum, gadolinium and/or lutetium ions (such as $Zn^{2+}$, $Ca^{2+}$, $Cd^{2+}$, $Y^{3+}$, $La^{3+}$, $Gd^{3+}$, $Lu^{3+}$ ions).

Therefore in an additional aspect, the present invention relates to a fluorescent probe comprising a metal complex of a compound of Formula I, wherein Formula I is as described in any of the embodiments set forth above. In one embodiment, the metal complex is a zinc, calcium, cadmium, yttrium, lanthanum, gadolinium and/or lutetium comlpex (e.g., a complex formed with $Zn^{2+}$, $Ca^{2+}$, $Cd^{2+}$, $Y^{3+}$, $La^{3+}$, $Gd^{3+}$ or $Lu^{3+}$ c). In another embodiment, the metal complex is a zinc or calcium complex (e.g., a complex formed with $Zn^{2+}$ or $Ca^{2+}$).

In a further aspect, the present invention relates to a method for detecting a metal ion comprising (i) exposing a sample to a compound of Formula I, and (ii) determining a change in fluorescence of said sample resulting from exposure to a compound of Formula I. In one embodiment, the metal ion is a zinc, calcium, cadmium, yttrium, lanthanum, gadolinium and/or lutetium ion (e.g., a $Zn^{2+}$, $Ca^{2+}$, $Cd^{2+}$, $Y^{3+}$, $La^{3+}$, $Gd^{3+}$ or $Lu^{3+}$ ion). In another embodiment, the metal ion is a zinc or calcium ion (e.g., a $Zn^{2+}$ or $Ca^{2+}$ ion).

In a further aspect, the present invention relates to a method for detecting a metal ion comprising (i) exposing a sample to a compound of Formula I, wherein said exposure results in a change in fluorescence of the sample, and (ii) detecting said change in fluorescence of said sample. In one embodiment, the metal ion is a zinc, calcium, cadmium, yttrium, lanthanum, gadolinium and/or lutetium ion (e.g., a $Zn^{2+}$, $Ca^{2+}$, $Cd^{2+}$, $Y^{3+}$, $La^{3+}$, $Gd^{3+}$ or $Lu^{3+}$ ion). In another embodiment, the metal ion is a zinc or calcium ion (e.g., a $Zn^{2+}$ or $Ca^{2+}$ ion).

In an additional aspect, the present invention relates to a fluorescent marker comprising a metal complex of compound of Formula I, wherein Formula I is as described in any of the embodiments set forth above. In one embodiment, the metal complex is a zinc, calcium, cadmium, yttrium, lanthanum, gadolinium and/or lutetium complex (e.g., a $Zn^{2+}$, $Ca^{2+}$, $Cd^{2+}$, $Y^{3+}$, $La^{3+}$, $Gd^{3+}$ or $Lu^{3+}$ complex). In another embodiment, the metal ion is a zinc or calcium complex (e.g., a $Zn^{2+}$ or $Ca^{2+}$ complex).

In an additional aspect, the present invention relates to a fluorescent reagent for a metal ion comprising a compound of Formula I, wherein Formula I is as described in any of the embodiments set forth above. In one embodiment, the metal ion is a zinc, calcium, cadmium, yttrium, lanthanum, gadolinium and/or lutetium ion (e.g., a $Zn^{2+}$, $Ca^{2+}$, $Cd^{2+}$, $Y^{3+}$, $La^{3+}$, $Gd^{3+}$ or $Lu^{3+}$ ion). In another embodiment, the metal ion is a zinc or calcium ion (e.g., a $Zn^{2+}$ or $Ca^{2+}$ ion).

In a further aspect, the present invention relates to a laser dye comprising a metal salt of a compound of Formula I, wherein Formula I is as described in any of the embodiments set forth above. In one embodiment, the metal salt is a $Zn^{2+}$, $Ca^{2+}$, $Cd^{2+}$, $Y^{3+}$, $La^{3+}$, $Gd^{3+}$ or $Lu^{3+}$ salt. In another embodiment, the metal ion is a $Zn^{2+}$ or $Ca^{2+}$ salt.

In another embodiment, the present invention relates to a fluorescent composition comprising (i) a fluorescent dye comprising a metal complex of a compound of Formula I, as described in any of the embodiments recited above, and (ii) a polymeric microparticle, wherein the amount of fluorescent dye is sufficient to make said microparticle fluorescent.

In certain embodiments, the polymer microparticle can be prepared from a variety of polymers including, but not limited to nitrocellulose, polystyrene (including high density polystyrene latexes such as brominated polystyrene), polymethylmethacrylate and other polyacrylic acids, polyacrylonitrile, polyacrylamide, polyacrolein, polydimethylsiloxane, polybutadiene, polyisoprene, polyurethane, polyvinylacetate, polyvinylchloride, polyvinylpyridine, polyvinylbenzylchloride, polyvinyltoluene, polyvinylidene chloride, and polydivinylbenzene. Preferably, the polymer microparticle is prepared from polystyrene or polyacrylamide. Preferred polymers are polystyrene-based, optionally copolymerized with a cross-linking agent such as divinylbenzene. Suitable particles that are also magnetic are available from, e.g., Dynal (Lake Success, N.Y.) and other sources.

In certain embodiments, the polymer microparticles can be manufactured in a variety of useful sizes and shapes. For example, the polymer microparticles may be spherical or irregular in shape, and range in size from about 0.01 micrometers to about 50 micrometers. In certain embodiments, the labeled microparticles are less than about 15 micrometers in diameter and are spherical. In other embodiments, the microparticle is a microsphere less than about 5 micrometers in diameter. In further embodiments, the microparticles may be of uniform size and/or shape or non-uniform.

In additional embodiments of any of the methods described herein, the compound of Formula I is not diethyl-7,7-difluoro-14-(1,4,7,10,13-pentaoxabenzoheptadecan-15-yl)-1,4,10,13-tetrahydro-1,4;10,13-bisethano-7-bora-7H-benzo[1,2-a;4,5-a']di-isoindole-5,9-dicarboxylate or diethyl-7,7-difluoro-14-(1,4,7,10,13-pentaoxabenzoheptadecan-15-yl)-7-bora-7H-benzo[1,2-a;4,5-a']diisoindole-5,9-dicarboxylate.

In additional embodiments of any of the methods described herein, the compound of Formula I is not a complex with boron. For example, the compound of Formula I is not a complex with a boron dihalide (e.g., boron difluoride).

Definitions

As used herein the term "halogen" means F, Cl, Br, and I.

The term "alkyl" means a substituted or unsubstituted saturated hydrocarbon radical which may be straight-chain or branched-chain and contains about 1 to about 20 carbon atoms, for instance 1 to 12 carbon atoms, such as 1 to 8 carbon atoms, e.g., 1 to 4 carbon atoms. Suitable alkyl groups include, but are not limited to, methyl, ethyl, propyl, isopropyl, butyl, sec-butyl, tert-butyl, pentyl, hexyl, heptyl, octyl, nonyl, decyl, undecyl, and dodecyl. Other examples of suitable alkyl groups include, but are not limited to, 1-, 2- or 3-methylbutyl, 1,1-, 1,2- or 2,2-dimethylpropyl, 1-ethylpropyl, 1-, 2-, 3- or 4-methylpentyl, 1,1-, 1,2-, 1,3-, 2,2-, 2,3- or 3,3-dimethylbutyl, 1- or 2-ethylbutyl, ethylmethylpropyl, trimethylpropyl, methylhexyl, dimethylpentyl, ethylpentyl, ethylmethylbutyl, dimethylbutyl, and the like.

Substituted alkyl groups are alkyl groups as described above which are substituted in one or more positions by, e.g., halogen, hydroxyl, amino, carboxy, and cyano, and combinations thereof (e.g., $CF_3$, $CHF_2$). The use of the term "halogenated alkyl" does not mean that "alkyl" cannot be substituted by one or more halogen atoms. The use of the term "hydroxyalkyl" does not mean that "alkyl" cannot be substituted by one or more hydroxyl atoms The term "alkenyl" means a substituted or unsubstituted hydrocarbon radical which may be straight-chain or branched-chain, which contains one or more carbon-carbon double bonds, and which may comprise about 1 to about 20 carbon atoms, such as 1 to 12 carbon atoms, for instance 1 to 6 carbon atoms. Suitable alkenyl groups include ethenyl, propenyl, butenyl, etc.

Substituted alkenyl groups are alkenyl groups as described above which are substituted in one or more positions by, e.g., halogen, hydroxyl, amino, carboxy, cyano, and combinations thereof.

The term "alkylene" means a linear saturated divalent hydrocarbon radical of one to six carbon atoms or a branched saturated divalent hydrocarbon radical of three to six carbon atoms unless otherwise stated e.g., methylene, ethylene, propylene, 1-methylpropylene, 2-methylpropylene, butylene, pentylene, and the like.

The term "alkynyl" means a substituted or unsubstituted aliphatic hydrocarbon radical which may be straight-chain or branched-chain and which contains one or more carbon-carbon triple bonds. Preferably the alkynyl group contains 2 to 15 carbon atoms, such as 2 to 12 carbon atoms, e.g., 2 to 8 carbon atoms. Suitable alkynyl groups include ethynyl, propynyl, butynyl, etc.

Substituted alkynyl groups are alkynyl groups as described above which are substituted in one or more positions by, e.g., halogen, hydroxyl, amino, carboxy, cyano, and combinations thereof.

The term "alkylcycloalkyl" means a cycloalkyl-alkyl-group, where cycloalkyl and alkyl are as described above.

The term "amino" means —$NH_2$.

The term "alkylamino" means —NH(alkyl), wherein alkyl is as described above.

The term "dialkylamino" means —N(alkyl)$_2$, wherein alkyl is as described above.

The term "alkylsulfonyl" means an —$SO_2$-alkyl group, wherein alkyl is as described above.

The term "alkylsulfinyl" means an —SO-alkyl group, wherein alkyl is as described above.

The term "aryl" means a substituted or unsubstituted aromatic monocyclic or bicyclic ring system comprising about 5 to about 14 carbon atoms, preferably about 6 to about 10 carbon atoms. Suitable aryl groups include, but are not limited to, phenyl, naphthyl, tetrahydronaphthyl, indanyl and indenyl.

Substituted aryl groups include the above-described aryl groups which are substituted one or more times by, for example, alkyl, alkenyl, alkynyl, cycloalkyl, alkylcycloalkyl, aryl, alkylaryl, heteroaryl, alkylheteroaryl, heterocycle, alkylheterocycle, to halogen, hydroxyl, cyano, alkoxy, arylaoxy, cycloalkyloxy, alkoxycarbonyl, carboxyl, amino, alkylamino, dialkylamino, —SH, thioalkyl, alkylsulfonyl, alkylsulfinyl, arylsulfonyl, arylsulfinyl, aminosulfonyl, aminosulfinyl, aroyl, acyl, and combinations thereof.

The term "arylsulfonyl" means an —$SO_2$-aryl group, wherein aryl is as described above.

The term "arylsulfinyl" means an —SO-aryl group, wherein aryl is as described above.

The term "carboxyl" means —C(O)OH.

The term "carboxyalkyl" means —C(O)O-alkyl, wherein alkyl is as described above.

The term "cycloalkyl" means a monocyclic, bicyclic or tricyclic nonaromatic saturated hydrocarbon radical having 3 to 10 carbon atoms, such as 3 to 8 carbon atoms, for example, 3 to 6 carbon atoms. Suitable cycloalkyl groups include, but are not limited to, cyclopropyl, cyclobutyl, cyclopentyl, cyclohexyl, cycloheptyl, cyclooctyl, norbornyl, 1-decalin, adamant-1-yl, and adamant-2-yl. Other suitable cycloalkyl groups include, but are not limited to, spiropentyl, bicyclo[2.1.0]pentyl, bicyclo[3.1.0]hexyl, spiro[2.4]heptyl, spiro[2.5]octyl, bicyclo[5.1.0]octyl, spiro[2.6]nonyl, bicyclo[2.2.0]hexyl, spiro[3.3]heptyl, bicyclo[4.2.0]octyl, and spiro[3.5]nonyl. Preferred cycloalkyl groups include cyclopropyl, cyclobutyl, cyclopentyl and cyclohexyl. The cycloalkyl group can be substituted, for example, by one or more halogens and/or alkyl groups.

The term "heteroaryl" means a substituted or unsubstituted aromatic monocyclic or multicyclic ring system comprising 5 to about 10 ring atoms, preferably 5 or 6 ring atoms, wherein at least one of the ring atoms is an N, O or S atom. Suitable heteroaryl groups include, but are not limited to furyl, thienyl, pyrrolyl, pyrazolyl, imidazolyl, pyridyl, pyrimidinyl, indolyl, quinolinyl, isoquinolinyl, naphthyridinyl and the like.

Substituted heteroaryl groups include the above-described heteroaryl groups which are substituted one or more times by, for example, alkyl, alkenyl, alkynyl, cycloalkyl, alkylcycloalkyl, aryl, alkylaryl, heteroaryl, alkylheteroaryl, heterocycle, alkylheterocycle, halogen, hydroxyl, cyano, alkoxy, arylaoxy, cycloalkyloxy, alkoxycarbonyl, carboxyl, amino, alkylamino, dialkylamino, —SH, thioalkyl, alkylsulfonyl, alkylsulfinyl, arylsulfonyl, arylsulfinyl, aminosulfonyl, aminosulfinyl, aroyl, acyl, and combinations thereof.

The term "heterocycle" means a substituted or unsubstituted non-aromatic mono- or multicyclic ring system comprising 3 to 10 atoms, preferably 5 or 6 atoms, wherein at least one of the ring atoms is an N, O or S atom. Suitable heterocyle groups include, but are not limited to tetrahydrofuranyl, tetrahydrothienyl, tetrahydropyranyl, dihydropyranyl, pyrrolidinyl, piperidinyl, piperazinyl, morpholinyl, isoxazolinyl, and the like Substituted heterocycle groups include the above-described heterocycle groups which are substituted one or more times by, for example, alkyl, alkenyl, alkynyl, cycloalkyl, alkylcycloalkyl, aryl, alkylaryl, heteroaryl, alkylheteroaryl, heterocycle, alkylheterocycle, halogen, hydroxyl, cyano, alkoxy, arylaoxy, cycloalkyloxy, alkoxycarbonyl, carboxyl, amino, alkylamino, dialkylamino, —SH, thioalkyl, alkylsulfonyl, alkylsulfinyl, arylsulfonyl, arylsulfinyl, aminosulfonyl, aminosulfinyl, aroyl, acyl, and combinations thereof.

The term "haloalkyl" means an alkyl group substituted by one or more halogens, for example, $CF_3$, $CF_2CF_3$, $CH_2F$, $CHF_2$, $CH_2Br$, and the like.

The term "hydroxyalkyl" means an alkyl group substituted by one or more hydroxyl groups, for example, $CH_2OH$, $CH_2CH_2OH$, and the like The term "aroyl" means an aryl-C(O)—, in which the aryl group is as previously described. Suitable aroyl groups include, but are not limited to, benzoyl and 1-naphthoyl.

The term "acyl" means an HC(O)—, alkyl-C(O)—, or cycloalkyl-C(O)—, in which the alkyl and cycloalkyl groups are as previously described.

The term "alkoxy" means alkyl-O- groups and in which the alkyl portion is in accordance with the previous discussion. Suitable alkoxy groups include, but are not limited to, methoxy, difluoromethoxy, trifluoromethoxy, ethoxy, n-propoxy, iso-propoxy, n-butoxy, t-butoxy, pentoxy, hexoxy, heptoxy, octoxy, and the like. For example, the alkoxy can be methoxy, difluoromethoxy, trifluoromethoxy or ethoxy.

The term "alkylaryl" refers to an aryl-alkyl-radical in which the aryl and alkyl portions are in accordance with the previous descriptions. Suitable examples include, but are not limited to, benzyl, 1-phenethyl, 2-phenethyl, phenpropyl, phenbutyl, phenpentyl, and napthylmethyl The term "alkylheterocycle" refers to a heterocycle-alkyl-group wherein the heterocycle and alkyl portions are in accordance with the previous discussions.

The term "alkylheteroaryl" refers to a heteroaryl-alkyl-group wherein the heteroaryl and alkyl portions are in accordance with the previous discussions. Suitable examples include, but are not limited to, pyridylmethyl, thiazolylmethyl, thienylmethyl, pyrimidinylmethyl, pyrazinylmethyl, and isoquinolinylmethyl The term "aryloxy" means an aryl-O— group, in which the aryl group is as previously described.

The term "alkylaryloxy" means aryl-alkyl-O—, in which the aryl and alkyl groups are as previously described.

The term "alkylthio" means an alkyl-S— group, in which the alkyl group is as previously described.

The term "arylthio" means an aryl-S— group, in which the aryl group is as previously described.

The term "alkoxycarbonyl" means an alkyl-O—CO— group, in which the alkyl group is as previously described.

The term "aminoalkyl" means a linear monovalent hydrocarbon radical of one to six carbon atoms or a branched monovalent hydrocarbon radical of three to six carbons substituted with at least one, preferably one or two, —NRR' where R is hydrogen, alkyl, or —COR$^a$ where R$^a$ is alkyl, and R' is selected from hydrogen, alkyl, hydroxyalkyl, alkoxyalkyl, aryl, aralkyl, heteroaryl, heteroaralkyl, or haloalkyl, e.g, aminomethyl, methylaminoethyl, 2-ethylamino-2-methylethyl, 1,3-diaminopropyl, dimethylaminoethyl, dimethylaminomethyl, diethylaminoethyl, acetylaminopropyl, and the like.

The term "amidoalkyl" means a linear monovalent hydrocarbon radical of one to six carbon atoms or a branched monovalent hydrocarbon radical of three to six carbons substituted with at least one, preferably one or two, —(CO)NRR' where R is hydrogen, alkyl, or —COR$^a$ where R$^a$ is alkyl, and R' is selected from hydrogen, alkyl, hydroxyalkyl, alkoxyalkyl, aryl, aralkyl, heteroaryl, heteroaralkyl, or haloalkyl, e.g., $CH_2CONH_2$, $CH_2CONH$alkyl (e.g., $CH_2CONHCH_3$), $CH_2CONH(alkyl)_2$ (e.g., $CH_2CON(CH_3)_2$), and the like.

The term aminosulfinyl" means a —SONRR' radical where R is independently hydrogen, alkyl, hydroxyalkyl, alkoxyalkyl, or aminoalkyl and R' is hydrogen, alkyl, cycloalkyl, cycloalkylalkyl, aryl, aralkyl, heteroaryl, heteroaralkyl, heterocyclyl, heterocyclylalkyl, hydroxyalkyl, alkoxyalkyl, or aminoalkyl as defined above, e.g., —$SONH_2$, methylaminosulfinyl, 2-dimethylaminosulfinyl, and the like.

The term "aminosulfonyl" means a —$SO_2NRR'$ radical where R is independently hydrogen, alkyl, hydroxyalkyl, alkoxyalkyl, or aminoalkyl and R' is hydrogen, alkyl, cycloalkyl, cycloalkylalkyl, aryl, aralkyl, heteroaryl, heteroaralkyl, heterocyclyl, heterocyclylalkyl, hydroxyalkyl, alkoxyalkyl, or aminoalkyl as defined above, e.g., —$SO_2NH_2$, methylaminosulfonyl, 2-dimethylaminosulfonyl, and the like.

The term "aryloxycarbonyl" means an aryl-O—C(O)— group, in which the aryl group is as previously described.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per practice in the art. Alternatively, "about" with respect to the compositions can mean plus or minus a range of up to 20%, preferably up to 10%, more preferably up to 5%.

The following examples are presented in order to more fully illustrate the preferred embodiments of the invention. They should in no way, however, be construed as limiting the broad scope of the invention. While the invention has been depicted and described by reference to exemplary embodiments of the invention, such a reference does not imply a limitation on the invention, and no such limitation is to be inferred. The invention is capable of considerable modification, alteration, and equivalents in form and function, as will occur to those ordinarily skilled in the pertinent arts having the benefit of this disclosure. The depicted and described embodiments of the invention are exemplary only, and are not exhaustive of the scope of the invention. Consequently, the invention is intended to be limited only by the spirit and scope of the appended claims, giving full cognizance to equivalence in all respects.

All references cited herein are hereby incorporated by reference in their entirety.

EXAMPLES

All starting materials are readily available, or may be prepared by one of ordinary skill as described in the art. For example, 2-ethoxycarbonyl-4,5,6,7-tetrahydroisoindole may be prepared according to O. S. Finikova et al., *J. Org. Chem.*, 69, 522-535, 2004; 2-tert-butoxycarbonyl-4,7-dihydroisoindole and bis-(3-ethoxycarbonyl-4,7-dihydro-2H-isoindolyl) methane may be prepared according to M. A. Filatov et al., *J. Org. Chem.*, 73, 4175-4185, 2008; and 2-ethoxycarbonyl-4, 9-dihydrobenzo[f]isoindole may be prepared according to O. S. Finikova et al., *J. Org. Chem.*, 70, 4617-4628, 2005.

Example 1

Synthesis of 5-Ar-2,2'-di(tert-butoxycarbonyl) dibenzo[b,g]dipyrrins

Synthesis of meso-Ar-2,2'-di(ethoxycarbonyl)octahydrodibenzo[b,g]dipyrrins

2-Ethoxycarbonyl-4,5,6,7-tetrahydroisoindole (0.39 g, 2 mmol), the appropriate aromatic aldehyde (ArCHO) (1 mmol), p-toluenesulfonic acid (0.002 g, 0 1 mmol) and tetra-n-butylammonium chloride (0.003 g, 0.1 mmol) were dissolved in dichloromethane (20 ml) and stirred at room temperature for 12 h. The reaction mixture was washed with water (1×20 ml), brine (1×20 ml), dried over anhydrous $Na_2SO_4$, and the solvent was evaporated in vacuo. The residue was dissolved in dry THF (10 ml) and 2,3-dichloro-5,6-dicyanobenzoquinone (DDQ, 0.23 g, 1 mmol) was added to the solution. The solution was stirred for 30 min at room temperature, diluted by dichloromethane (50 ml), washed by 10% aqueous $Na_2SO_3$ (2×20 ml), brine (1×20 ml), dried over anhydrous $Na_2SO_4$, and the solvent was evaporated in vacuo. The residue was chromatographed on silica gel column using dichloromethane as the eluent. The product was additionally purified by recrystallization from petroleum ether.

Ar=4-MeO2C—$C_6H_4$: orange solid, yield 0.46 g, 86%, m. p. 185-186 C. $^1$H NMR (400 MHz, $CDCl_3$) $\delta_H$, ppm 13.16 (br. s, 1H), 8.16 (m, 2H), 7.40 (m, 2H), 4.41 (m, 4H), 4.00 (s, 3H), 2.70 (m, 4H), 1.30-1.65 (overlapp. m, 18H).

Ar=4-Br—C$_6$H$_4$: orange solid, yield 0.495 g, 90%, m. p. 188-190 C. $^1$H NMR (400 MHz, CDCl$_3$) δ$_H$, ppm 13.04 (br. s, ~1H), 7.63 (m, 2H), 7.19 (m, 2H), 4.41 (q, 4H, J=6.95 Hz), 2.71 (m, 4H), 1.55-1.65 (overlapp. m, 8H), 1.40-1.47 (overlap. m, 10H).

Synthesis of 2,2'-di(ethoxycarbonyl)dibenzo[b,g]dipyrrin

Bis(3-ethoxycarbonyl-4,7-dihydro-2H-isoindolyl)methane (0.20 g, 0.5 mmol) and DDQ (0.34 g, 1.5 mmol) were dissolved in dry THF (10 ml). The solution was stirred for 30 min at room temperature, diluted by dichloromethane (DCM) (50 ml), washed with 10% aqueous Na$_2$SO$_3$ (2×20 ml), brine (1×20 ml), dried over anhydrous Na2SO4, and the solvent was evaporated in vacuum. The residue was chromatographed on silica gel column using DCM as the eluent. The product was additionally purified by recrystallization from CH2Cl2-MeOH mixture to yield dark blue crystals: 0.18 g, 93%, m. p. 168-170 C. $^1$NMR (400 MHz, CDCl$_3$) δ$_H$, ppm 9.3 (br. s, 1H), 8.16 (m, 2H), 7.81 (m, 2H), 7.57 (s, 1H), 7.38 (overlapp m, 4H), 4.53 (q, 4H, I=7.07 Hz), 1.55 (t, 6H, J=7.07 Hz). $^{13}$C NMR (100 MHz, CDCl3) δ$_C$, ppm 161.6, 138.1, 135.5, 135.3, 131.3, 127.2, 126.7, 122.9, 119.1, 116.5, 61.2, 14.5.

Synthesis of 5-Ar-2,2'-di(tert-butoxycarbonyl) dibenzo[b,g]dipyrrins 2-tert-butoxycarbonyl-4,7-di-2H-hydroisoindole (0.44 g, 2 mmol), aromatic aldehyde (ArCHO) (1 mmol), p-toluenesulfonic acid (0.002 g, 0.1 mmol) and tetra-n-butylammonium chloride (0.003 g, 0.1 mmol) were dissolved in DCM (20 ml) and stirred at room temperature for 12 h. The reaction mixture was washed with water (1×20 ml), brine (1×20 ml), dried over anhydrous Na$_2$SO$_4$, and the solvent was evaporated to dryness. The residue was dissolved in dry THF (10 ml), and 2,3-dichloro-5,6-dicyanobenzoquinone (DDQ, 0.68 g, 3 mmol) was added to the solution. The resulting mixture was stirred for 30 min at room temperature, diluted by DCM (50 ml), washed by 10% aqueous Na$_2$SO$_3$ (2×20 ml), brine (1×20 ml), dried over anhydrous Na$_2$SO$_4$, and the solvent was evaporated in vacuum. The residue was chromatographed on silica gel column using DCM as the eluent. The product was additionally purified by recrystallization from CH$_2$Cl$_2$-MeOH mixture.

Ar=4-MeO$_2$C—C$_6$H$_4$: purple crystals, yield 0.50 g, 87%, m. p. 248-250 C. $^1$H NMR (400 MHz, CDCl$_3$) δ$_H$, ppm 14.79 (br. s, 1H), 8.36 (d, 2H, J=8.08 Hz), 8.16 (d, 2H, J=8.08 Hz), 7.66 (d, 2H, J=8.08 Hz), 7.23 (m, 2H), 6.97 (m, 2H), 6.09 (d, 2H, J=8.34 Hz), 4.08 (s, 3H), 1.78 (s, 18H). $^{13}$C NMR (100 MHz, CDCl$_3$) δ$_C$, ppm 166.7, 161.0, 141.3, 139.5, 137.5, 135.4, 133.9, 131.3, 131.1, 130.6, 129.6, 126.9, 125.9, 123.0, 121.7, 82.5, 52.5, 28.4.

Ar=4-Br—C$_6$H$_4$: dark-brown crystals, yield 0.55 g, 92%, m. p. 248-250 C. $^1$H NMR (400 MHz, CDCl$_3$) δ$_H$, ppm 14.76 (br. s, 1H), 8.15 (d, 2H, J=8.21 Hz), 7.81 (d, 2H, J=8.21 Hz), 7.42 (d, 2H, J=8.21 Hz), 7.23 (m, 2H), 7.02 (m, 2H), 6.19 (d, 2H, J=8.21 Hz), 1.79 (s, 18H). $^{13}$C NMR (100 MHz, CDCl$_3$) δ$_C$, ppm 161.0, 139.5, 137.3, 135.5, 134.2, 132.8, 131.4, 131.1, 127.0, 125.9, 123.7, 123.1, 121.8, 82.6, 28.4.

Ar=2-HO—C$_6$H$_4$: purple crystals, yield 0.19 g, 35%, m. p.>280 C (decomp). $^1$H NMR (400 MHz, CDCl$_3$) δ$_H$, ppm 14.74 (br. s, 1H), 8.15 (d, 2H, J=7.96 Hz), 7.62 (m, 2H), 7.37 (m, 2H), 7.23 (m, 2H), 7.04 (m, 2H), 6.36 (m, 2H), 5.03 (br. s, 1H), 1.71 (s, 18H).

Ar=2-thienyl: dark-green crystals, yield 0.43 g, 82%, m. p. 252-253° C. $^1$H NMR (400 MHz, CDCl$_3$) δ$_H$, ppm 14.60 (br. s, 1H), 8.16 (m, 2H), 7.73 (m, 2H), 7.37 (m, 1H), 7.29 (m, 1H), 7.26 (m, 2H), 7.08 (m, 2H), 6.35 (m, 2H), 1.77 (s, 18H). $^{13}$C NMR (100 MHz, CDCl$_3$) δ$_C$, ppm 161.0, 139.6, 135.5, 131.4, 128.9, 128.1, 128.0, 127.0, 126.1, 122.97, 122.03, 82.4, 28.4.

Ar=3,5-tertBu$_2$-C$_6$H$_3$: purple crystals, yield 0.56 g, 88%, m. p. 208-210° C. $^1$H NMR (400 MHz, CDCl$_3$) δ$_H$, ppm 14.7 (br. s, 1H), 8.15 (m, 2H), 7.72 (t, 1H, J=1.77 Hz, 7.36 (d, 2H, J=1.77 Hz), 7.21 (m, 2H), 6.94 (m, 2H), 6.16 (m, 2H), 1.77 (s, 18H), 1.37 (s, 18H). $^{13}$C NMR (100 MHz, CDCl$_3$) δ$_C$, ppm 161.2, 152.1, 140.5, 138.9, 135.9, 135.5, 134.7, 131.4, 130.8, 126.4, 125.6, 123.7, 122.7, 122.4, 122.2, 82.2, 35.2, 31.5, 28.4.

Synthesis of meso-(4-MeO$_2$C—C$_6$H$_4$)-2,2'-di (ethoxycarbonyl)dinaphtho[2,3-b,g]dipyrrin 2,2'-di (ethoxycarbonyl)dinaphtho[2,3-b,g]dipyrrin 2-Ethoxycarbonyl-4,9-dihydrobenzo-isoindole (2.41 g, 10 mmol), dimethoxymethane (0.38 g, 5 mmol), and PTSA (0.095 g, 0.5 mmol) were dissolved in acetic acid (50 ml), and the mixture was stirred for 12 h at room temperature. The reaction mixture was then diluted by water (200 ml), and the precipitate was filtered off on a glass filter, dried over P$_2$O$_5$ in vacuum, and recrystallized from EtOH. 2,9-dnethoxycarbonyl)dinaphtho[2,3-b,g]dipyrromethane was obtained as a white solid, yield 2.35 g, 95%, m. p. 155-156 C.

$^1$H NMR (400 MHz, CDCl$_3$) δ$_H$, ppm 10.91 (br. s., 2H), 7.17-7.26 (m, 4H), 7.06-7.14 (m, 4H), 4.25 (q, 4H), 4.03 (s, 4H), 3.89 (s, 2H), 3.83 (s, 4H), 1.31 (t, 6H). $^{13}$C NMR (100 MHz, CDCl$_3$) δ$_C$, ppm 161.77, 135.29, 134.58, 129.36, 129.19, 129.00, 125.92, 125.77, 116.25, 116.10, 59.53, 28.52, 26.52, 22.42, 14.69.

A mixture of 2,9-di(ethoxycarbonyl)dinaphtho[2,3-b,g] dipyrromethane (0.25 g, 0.5 mmol) and DDQ (0.34 g, 1.5 mmol) were dissolved in dry THF (10 ml). The mixture was stirred for 30 min at room temperature, diluted by DCM (50 ml), washed with 10% aqueous Na$_2$SO$_3$ (2×20 ml), brine (1×20 ml), dried over anhydrous Na$_2$SO$_4$, and the solvent was evaporated in vacuum. The residue was dissolved in dry THF (10 ml) and DDQ (0.34 g, 1.5 mmol) was added. The mixture was stirred for 30 min, followed by a work up as described above. The residue was chromatographed on a silica gel column using DCM as the eluent, and the product was re-crystallized from CH$_2$Cl$_2$-MeOH mixture to yield dark-blue crystals: yield 0.19 g, 83%, m. p. 246-248 C.

$^1$H NMR (400 MHz, CDCl$_3$) δ$_H$, ppm 8.70 (s, 2H), 8.37 (s, 2H), 7.96 (m, 4H), 7.78 (s, 1H), 7.47 (m, 4H), 4.59 (q, 4H, J=7.07 Hz), 1.59 (t, 6H, J=7.07 Hz).

meso-(4-MeO$_2$C—C$_6$H$_4$)-2,2'-di(ethoxycarbonyl) dinaphtho[2,3-b,g]dipyrrin 2-ethoxycarbonyl-4,9-dihydrobenzo[f]isoindole (0.48 g, 2 mmol), p-methoxycarbonyl benzaldehyde (0.16 g, 1 mmol), PTSA (0.002 g, 0.1 mmol), and tetra-n-butylammonium chloride (0.003 g, 0.1 mmol) were dissolved in DCM (20 ml) and stirred ar room temperature under Ar for 12 h. The mixture was washed with water (1×20 ml), brine (1×20 ml), dried over anhydrous Na$_2$SO$_4$, and the solvent was evaporated to dryness. The residue was dissolved in dry THF (20 ml), and 2,3-dichloro-5,6-dicyanobenzoquinone (DDQ, 0.68 g, 3 mmol) was added to the solution. The mixture was stirred for 1 h at room temperature, concentrated in vacuum, diluted by DCM (50 ml), carefully washed by 10% aqueous Na$_2$SO$_3$ (2×20 ml), brine (1×20 ml), dried over anhydrous $Na_2SO_4$, and the solvent was evaporated dryness. The residue was dissolved in dry THF (20 ml) and treated once again with DDQ in the same manner. The solid was chromatographed on a silica gel column using DCM as the eluent. The product was additionally purified by re-crystallization from MeOH—$CH_2Cl_2$, yielding a to dark-blue solid: 0.49 g, 78%, m. p. 262-264 C.

$^1$H NMR (400 MHz, $CDCl_3$) $\delta_H$, ppm 15.18 (br. s, 1H), 8.74 (s, 2H), 8.50 (d, 2H, J=7.83 Hz), 7.92 (d, 2H, J=7.83 Hz), 7.83 (d, 2H, J=7.53 Hz), 7.30-7.45 (overlapp. m, 5H), 6.64 (s, 2H), 4.66 (q, 4H, J=7.07 Hz), 4.17 (s, 3H), 1.64 (t, 6H, J=7.07 Hz). $^{13}$C NMR (100 MHz, $CDCl_3$) $\delta_C$, ppm 161.7, 141.8, 137.1, 134.1, 132.5, 132.2, 132.0, 131.0, 130.9, 130.2, 129.7, 129.3, 129.2, 129.0, 127.3, 126.5, 126.2, 125.9, 123.7, 122.2, 121.1, 61.4, 52.6, 28.5, 27.7.

Example 2

Complexation of 2,2'-Disubstituted Dipyrrins with Metal Ions and Preparation of Samples for Photophysical Measurements In a typical experiment, a metal salt (~100 mg) was added to a solvent (~3 ml), followed by the addition of a few drops of a highly concentrated solution of the 2,2'-disubstituted dipyrrin ligand. The resulting slurry was rigorously stirred for about 30 seconds, then optionally filtered through a cotton cloth.

Figure 6:
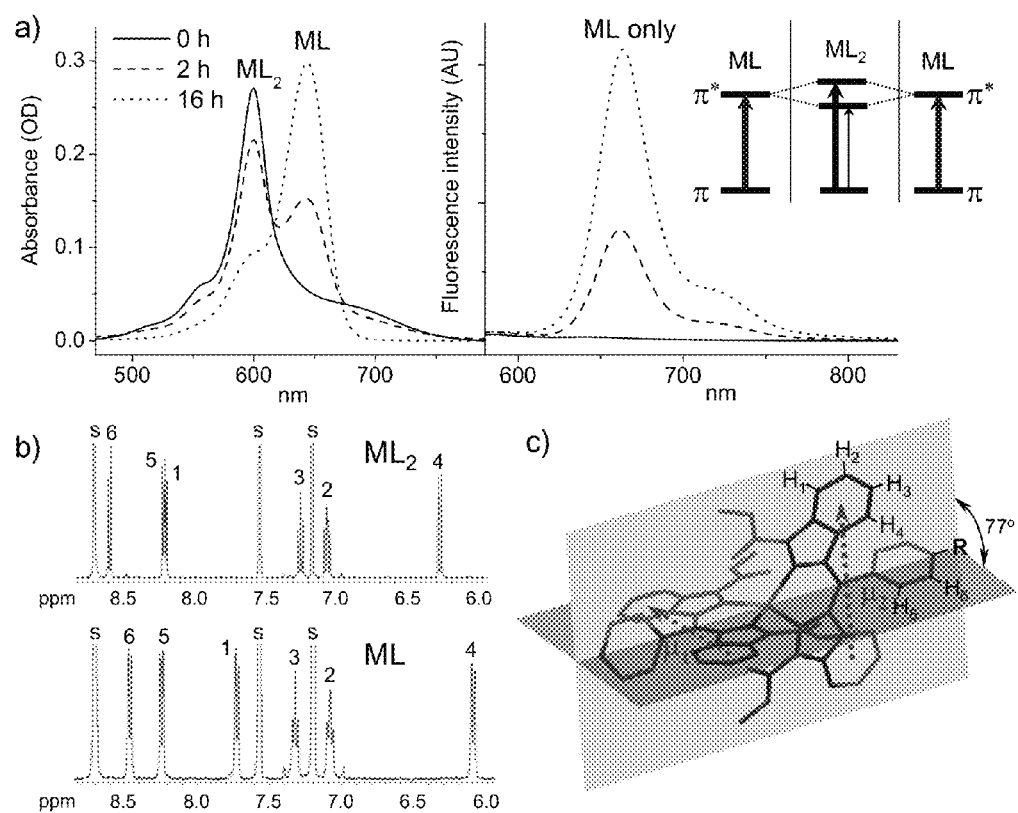
FIG. 6 depicts (a) changes in absorption (left) and emission (right) spectra of ZnL$_2$ (L=meso-(4-(MeO$_2$C)C$_6$H$_4$)-2,2'-diethoxycarbonyldibenzopyrromethene) upon addition of excess ZnCl$_2$; (b) $^1$H NMR spectra of ZnL$_2$ and ZnL metal complex forms; and (c) ab initio calculated optimized structure (DFT/B3LYP/6-31G(d)) of ZnL$_2$.

For example, meso-(4-$MeO_2C$—$C_6H_4$)-2,2' di(ethoxycarbonyl)dibenzo[b,g]dipyrrin was mixed with an excess of zinc acetate ($Zn(OAc)_2$) in acetone. A dark blue blue solution resulted. The absorption and emission spectra of this soliution are shown in FIG. 3 ($\lambda$max~642 nm). Upon standing overnight, dark crystals of the homoleptic $ZnL_2$ complex (L=meso-(4-$MeO_2C$—$C_6H_4$)-5,5 dnethoxycarbonyl)dibenzo[b,g]dipyrrin) precipitated form the solution. The $ZnL_2$ crystals were found to be highy soluble in toluene, methylene chloride and pyridine, but were poorly soluble in alcohols, acetone and DMF. A pyridine solution of $ZnL_2$ compound showed no fluorescence. Upon addition of an excess of $ZnCl_2$, however, the original spectrum (as shown in FIG. 3) slowly redeveloped ($\lambda$max~642 nm). After approximately 16 hours, the original spectrum fully developed and fluorescence was fully regained. See FIG. 6a. $^1$H NMR spectra for a sample of $ZnL_2$ in $d_5$ pyridine, before and after addition of an excess of $ZnCl_2$ are shown in FIG. 6b. The ab initio computed model (DFT/B3LYP/6-31G(d)) of the $ZnL_2$ complex is shown in FIG. 6c.

Figure 7:
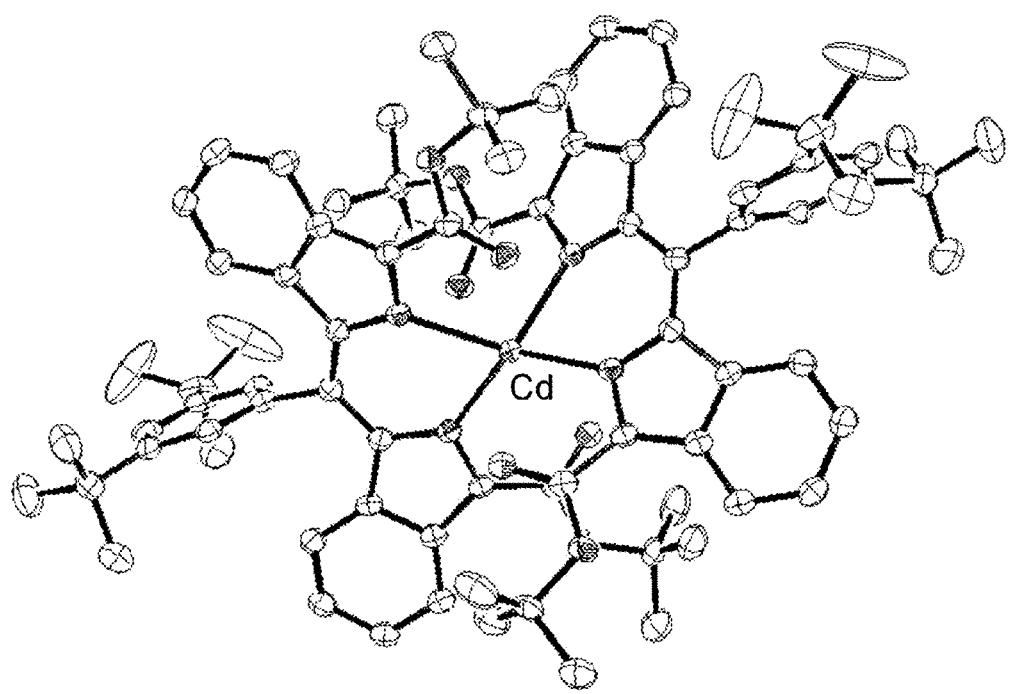
FIG. 7 depicts the X-ray crystallographic structure of Cd(meso-Ar-2,2'-di-tert-butoxycarbonyl-dibenzopyrromethene)$_2$ (Ar=3,5-tBu$_2$C$_6$H$_3$).

Cd(meso-Ar-2,2'-di-tert-butoxycarbonyl-dibenzopyrromethene)$_2$ (Ar=3,5-$tBu_2C_6H_3$) was prepared in a similar manner as described above. FIG. 7 shows the X-ray crystallographic structure of Cd(meso-Ar-2,2'-di-tert-butoxycarbonyl-dibenzopyrromethene)$_2$ (Ar=3,5-$tBu_2C_6H_3$).

To prepare a sample suitable for photophysical measurement, a solution of a metal complex was diluted to achieve a concentration suitable for fluorescence quantum yield measurements (<0.10 OD at the $\lambda_{ex}$). Alternatively, a metal salt was added to a solution of a 2,2'-disubstituted dipyrrin which had already been diluted to a concentration suitable for optical measurements. The mixture was kept for several minutes, filtered and transferred to the measurement cell.

Spectroscopic grade solvents were used in the preparation of metal complex samples for photophysical measurements. In certain cases, a solution of a free-base 2,2'-disubstituted dipyrrin ligand was treated with a small amount of trifluoracetic acid (TFA) in order to prevent complex formation with trace amount of metal impurities contained in the solvent. However, in certain solvents (e.g. MeOH) relatively pure samples of free-base ligands could be obtained without the TFA treatment.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A fluorescent marker comprising a metal complex having a metal and a compound of Formula I:

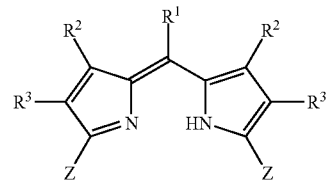

I wherein $R^1$ is H, cycloalkyl, aryl or heteroaryl;

$R^2$ and $R^3$ are fused, in each case, to form a cycloalkenyl or an aryl group; and Z is $CO_2R^x$, $C(O)R^x$, or $CON(R^x)_2$, wherein $R^x$ is, in each case independently, H or alkyl;

wherein said metal complex does not include boron, and wherein said metal complex is fluorescent.

2. The fluorescent marker of claim 1, wherein Z is $CO_2R^x$ or $C(O)R^x$.

3. The fluorescent marker of claim 2, wherein Z is $CO_2R^x$.

4. The fluorescent marker of claim 3, wherein Z is $CO_2CH_3$ or $CO_2Et$.

5. The fluorescent marker of claim 1, wherein $R^1$ is H or aryl.

6. The fluorescent marker of claim 5, wherein $R^1$ is aryl.

7. The fluorescent marker of claim 1, wherein $R^2$ and $R^3$ are fused to form an aryl group.

8. The fluorescent marker of claim 7, wherein $R^2$ and $R^3$ are fused to form a benzo group.

9. The fluorescent marker of claim 7, wherein $R^2$ and $R^3$ are fused to form a naphtho group.

10. The fluorescent marker of claim 1, wherein Formula I is represented by subformula Ia, Ib or Ic:

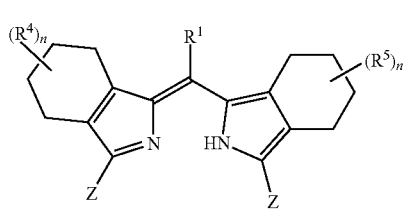

Ia

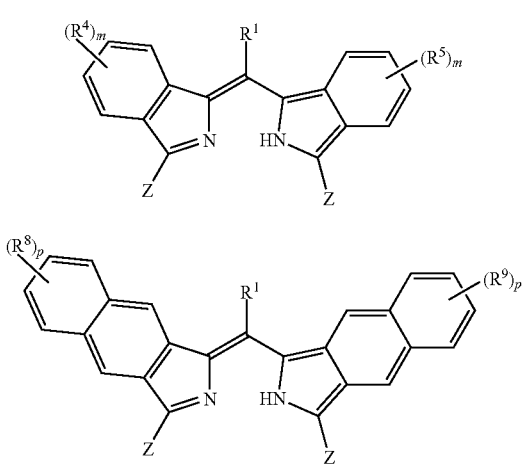

wherein
$R^4$, $R^5$, $R^6$, $R^7$, $R^8$ and $R^9$ are each, independently, hydrogen, halogen, hydroxyl, cyano, nitro, amino, alkylamino, dialkylamino, alkyl, alkenyl, alkynyl, cycloalkyl, aryl, alkylaryl, heteroaryl, alkylheteroaryl, heterocycle, alkylheterocycle, acyl, alkoxy, alkythio, arylthio, aminoalkyl, amidoalkyl, alkylsulfinyl, alkylsulfonyl, alkoxy, aryloxy or acyl,
n is, in each case, 1, 2, 3, 4, 5, 6, 7 or 8;
m is, in each case, 1, 2, 3 or 4; and
p is, in each case, 1, 2, 3, 4, 5 or 6.

11. The fluorescent marker of claim 1, wherein said metal complex is selected from the group consisting of a beryllium, magnesium, nickel, zinc, platinum, calcium, cadmium, mercury, yttrium, lanthanum, gadolinium, scandium, ytterbium and lutetium complex.

12. The fluorescent marker of claim 1, wherein said metal complex is selected from the group consisting of a nickel, zinc, lithium, sodium, potassium, calcium, cadmium, silver, manganese, mercury, yttrium, lanthanum, gadolinium, ytterbium and lutetium complex.

13. The fluorescent marker of claim 12, wherein said metal complex is selected from the group consisting of a zinc, calcium, cadmium, ytterbium, lanthanum, gadolinium and lutetium complex.

14. The fluorescent marker of claim 3, wherein said metal complex is a calcium complex or a zinc complex.

15. The fluorescent marker of claim 1, wherein Formula I is selected from:
meso-(phenyl)-2,2'-diethoxycarbonyl-ditetracyclohexenodipyrrin (1);
meso-(4-methoxyphenyl)-2,2'-diethoxycarbonyl-ditetracyclohexenodipyrrin (2);
meso-(3,5-dimethoxycarbonylphenyl)-2,2'-diethoxycarbonyl-ditetracyclohexenodipyrrin (2a);
meso-(3,5-ditertbuthylpheny)-2,2'-diethoxycarbonyl-ditetracyclohexenodipyrrin (2b);
meso-(4-bromophenyl)-2,2'-diethoxycarbonyl-ditetracyclohexenodipyrrin (2c);
meso-(4-chloroophenyl)-2,2'- diethoxycarbonyl-ditetracyclohexenodipyrrin (2e);
meso-(4-methoxyphenyl)-2,2'-diethoxycarbonyl-ditetracyclohexenodipyrrin (2f);
2,2'-ditertbutoxycarbonyl-ditetracyclohexenodipyrrin (3);
meso-(phenyl)-2,2'-tertbutoxycarbonyl-ditetracyclohexenodipyrrin (4);
meso-(4-methoxycarbonylphenyl)-2,2'-tertbutoxycarbonyl-ditetracyclohexenodipyrrin (4a);
meso-(3,5-di-tertbutylphenyl)-2,2'-tertbutoxycarbonyl-ditetracyclohexenodipyrrin (4b);
meso-(4-bromophenyl)-2,2'-tertbutoxycarbonyl-ditetracyclohexenodipyrrin (4c);
meso-(4-chlorophenyl)-2,2'-tertbutoxycarbonyl-ditetracyclohexenodipyrrin (4d);
meso-(4-methoxycarbonylphenyl)- 2,2'-diethoxycarbonyl-di(dihydroxytetracyclohexeno) dipyrrin (5);
2,2'-diethoxycarbonyl-dibenzodipyrrin (6);
meso-(phenyl)-2,2'-diethoxycarbonyl-dibenzodipyrrin (7);
meso-(4-methoxycarbonylphenyl)-2,2'-diethoxycarbonyl-dibenzodipyrrin (7a);
meso-(3,5-dimethoxycarbonylphenyl)-2,2'-diethoxycarbonyl-dibenzodipyrrin (7b);
meso-(3,5-ditertbutylphenyl)-2,2'-diethoxycarbonyl-dibenzodipyrrin (7c);
meso-(4-bromophenyl)-2,2'-diethoxycarbonyl-dibenzodipyrrin (7d);
meso-(4-chlorophenyl)-2,2'-diethoxycarbonyl-dibenzodipyrrin (7e);
meso-(4-methoxyphenyl)-2,2'-diethoxycarbonyl-dibenzodipyrrin (7f);
2,2'- tertbutoxycarbonyl-dibenzodipyrrin (8);
meso-(phenyl)-2,2'-tertbutoxycarbonyl-dibenzodipyrrin (9);
meso-(4-methoxycarbonylphenyl)-2,2'-tertbutoxycarbonyl-dibenzodipyrrin (9a);
meso-(3,5-ditertbutylphenyl)-2,2'-tertbutoxycarbonyl-dibenzodipyrrin (9b);
meso-(4-bromophenyl)-2,2'-tertbutoxycarbonyl-dibenzodipyrrin (9c);
meso-(4-chlorophenyl)-2,2'-tertbutoxycarbonyl-dibenzodipyrrin (9d);
2,2'-diethoxycarbonyl-dinaphthodipyrrin (10);
meso-(phenyl)-2,2'-diethoxycarbonyl-dinaphthodipyrrin (11);
meso-(4-methoxycarbonylphenyl)-2,2'-diethoxycarbonyl-dinaphthodipyrrin (11a);
meso-(3,5-dimethoxycarbonylphenyl)-2,2'-diethoxycarbonyl-dinaphthodipyrrin (11b);
meso-(3,5-ditertbutylphenyl)-2,2'-diethoxycarbonyl-dinaphthodipyrrin (11c);
meso-(4-bromophenyl)-2,2'-diethoxycarbonyl-dinaphthodipyrrin (11d);
meso-(4-chlorophenyl)-2,2'-diethoxycarbonyl-dinaphthodipyrrin (11e);
meso-(4-methoxyphenyl)-2,2'-diethoxycarbonyl-dinaphthodipyrrin (11f);
2,2'- tertbutoxycarbonyl-dinaphthodipyrrin (12);
meso-(phenyl)-2,2'-tertbutoxycarbonyl-dinaphthodipyrrin (13);
meso-(4-methoxycarbonylphenyl)-2,2'-tertbutoxycarbonyl-dinaphthodipyrrin (13a);
meso-(3,5-ditertbutylphenyl)-2,2'-tertbutoxycarbonyl-dinaphthodipyrrin (13b);
meso-(4-bromophenyl)-2,2'-tertbutoxycarbonyl-dinaphthodipyrrin (13c); and
meso-(4-chlorophenyl)-2,2'-tertbutoxycarbonyl-dinaphthodipyrrin (13d).

16. The fluorescent marker of claim 1, wherein Formula I is selected from:
2,2'-diethoxycarbonyl-dibenzodipyrrin (6);
meso-(phenyl)-2,2'-diethoxycarbonyl-dibenzodipyrrin (7);

meso-(4-methoxycarbonylphenyl)-2,2'-diethoxycarbonyl-dibenzodipyrrin (7a);
meso-(3,5-dimethoxycarbonylphenyl)-2,2'-diethoxycarbonyl-dibenzodipyrrin (7b);
meso-(3,5-ditertbutylphenyl)-2,2'-diethoxycarbonyl-dibenzodipyrrin (7c);
meso-(4-bromophenyl)-2,2'-diethoxycarbonyl-dibenzodipyrrin (7d);
meso-(4-chlorophenyl)-2,2'-diethoxycarbonyl-dibenzodipyrrin (7e);
meso-(4-methoxyphenyl)-2,2'-diethoxycarbonyl-dibenzodipyrrin (7f);
2,2'- tertbutoxycarbonyl-dibenzodipyrrin (8);
meso-(phenyl)- 2,2'-tertbutoxycarbonyl-dibenzodipyrrin (9);
meso-(4-methoxycarbonylphenyl)-2,2'-tertbutoxycarbonyl-dibenzodipyrrin (9a);
meso-(3,5-ditertbutylphenyl)- 2,2'-tertbutoxycarbonyl-dibenzodipyrrin (9b);
meso-(4-bromophenyl)-2,2'-tertbutoxycarbonyl-dibenzodipyrrin (9c);
meso-(4-chlorophenyl4)-2,2'-tertbutoxycarbonyl-dibenzodipyrrin (9d);
2,2'-diethoxycarbonyl-dinaphthodipyrrin (10);
meso-(phenyl)-2,2'-diethoxycarbonyl-dinaphthodipyrrin (11);
meso-(4-methoxycarbonylphenyl)-2,2'-diethoxycarbonyl-dinaphthodipyrrin (11a);
meso-(3,5-dimethoxycarbonylphenyl)-2,2'-diethoxycarbonyl-dinaphthodipyrrin (11b);
meso-(3,5-ditertbutylphenyl)-2,2'-diethoxycarbonyl-dinaphthodipyrrin (11c);
meso-(4-bromophenyl)-2,2'-diethoxycarbonyl-dinaphthodipyrrin (11d);
meso-(4-chlorophenyl)-2,2'-diethoxycarbonyl-dinaphthodipyrrin (11e);
meso-(4-methoxyphenyl)-2,2'-diethoxycarbonyl-dinaphthodipyrrin (11f;
2,2'- tertbutoxycarbonyl-dinaphthodipyrrin (12);
meso-(phenyl)-2,2'-tertbutoxycarbonyl-dinaphthodipyrrin (13);
meso-(4-methoxycarbonylphenyl)-2,2'-tertbutoxycarbonyl-dinaphthodipyrrin (13a);
meso-(3,5-ditertbutylphenyl)- 2,2'-tertbutoxycarbonyl-dinaphthodipyrrin (13b);
meso-(4-bromophenyl)-2,2'-tertbutoxycarbonyl-dinaphthodipyrrin (13c); and
meso-(4-chlorophenyl)-2,2'-tertbutoxycarbonyl-dinaphthodipyrrin (13d).

* * * * *